United States Patent
Holla et al.

(10) Patent No.: US 7,094,795 B2
(45) Date of Patent: Aug. 22, 2006

(54) PROCESS FOR PREPARING THE ENANTIOMERIC FORMS OF CIS-CONFIGURED 1,3-CYCLOHEXANEDIOL DERIVATIVES

(75) Inventors: Wolfgang Holla, Kelkheim (DE); Stephanie Keil, Hofheim (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 0 days.

(21) Appl. No.: 10/789,053

(22) Filed: Feb. 27, 2004

(65) Prior Publication Data

US 2004/0209931 A1 Oct. 21, 2004

Related U.S. Application Data

(60) Provisional application No. 60/487,416, filed on Jul. 15, 2003.

(30) Foreign Application Priority Data

Feb. 27, 2003 (DE) ................ 103 08 350

(51) Int. Cl.
*A61K 31/42* (2006.01)
*C07D 263/34* (2006.01)
(52) U.S. Cl. ..................... 514/374; 548/236
(58) Field of Classification Search ........ 514/374; 548/236

See application file for complete search history.

(56) References Cited

U.S. PATENT DOCUMENTS 6,624,185 B1 * 9/2003 Glombik et al. ............ 514/374
6,884,812 B1 * 4/2005 Glombik et al. ............ 514/374

FOREIGN PATENT DOCUMENTS

WO    WO 01/57232    8/2001
WO    WO 03/020269    3/2003

OTHER PUBLICATIONS

Bajwa Joginder S. et al., In-situ generation of Et3SiBr from BiBr3 and Et3SiH and its use in preparation of dialkyl ethers, Tetrahedron Letters, (2002), vol. 43, pp. 6709-6713.
Bartels Birgit et al., A Selectivity Study Of Activated Ketal Reduction With Borane Dimethyl Sulfide, Journal of Organic Chemistry, (1993), vol. 58, pp. 6756-6765.
Brinkman John A. et al., Trifluoromethyl-Substituted Indenyl Rhodium and Iridium Complexes Are Highly Selective Catalysts for Directed Hydroboration Reactions, Organic Letters, (2000), vol. 2, No. 7, pp. 981-983.

Carda M. et al., Enantiotoposelective Ple-Catalyzed Hydrolysis of Cis-5-Substituted- 1,3-Diacyloxycyclohexanes. Preparation of Some Useful Chiral Building Blocks, Tetrahedron Asymmetry, (1990), vol. 1, No. 1, pp. 17-20.
Crotti Paolo et al., Regiochemical Control of the Ring Opening of 1,2-Epoxides by Means of Chelating Process. Part 14: Regioselectivity of the Opening Reactions with MeOH of Remote O-Substituted 1,2-Epoxycyclohexanes under Gas-Phase Operating Conditions, Tetrahedron, (2000), vol. 56, pp. 7513-7524.
Davies William et al., The Chlorination and Bromination of the Toluic Acids and the Preparation of the Phthaladehydic Acids, Journal of Chemical Soc., (1922), vol. 121, pp. 2202-2215.
Dumortier L. et al., Revision of the enantiotoposelective PLE-catalyzed hydrolysis of cis-5-substituted- 1,2-diacyloxycyclohexanes, Tetrahedron: Asymmetry, (1991), vol. 2, No. 8, pp. 789-792.
Garrett Christine E. et al., Exploiting n5—to n3 Indenyl Ring Slippage to Access a Directed Reaction: Ether-Directed, Rhodium-Catalyzed Olefin Hydroboration, Journal of Organic Chemistry, (1998), vol. 63, pp. 1370-1371.
Goto Yoshinobu et al., Studies on Azole Compounds III Reactions of Oxazole N-Oxides with Phosphoryl Chloride and Acetic Anhydride, Chem. Pharm. Bull, (1971), vol. 19, No. 10, pp. 2050-2057.
Gruber-Khadjawi Mandana et al., Chemoenzymatic Methods for the Preparation of Optically Active Cyclic Polyazido Alcohols from Easily Available Achiral Starting Materials, Tetrahedron Asymmetry, (1996), vol. 7, No. 3, pp. 807-814.
Hubgerhoff Benno et al., Combining Lipase-Catalyzed Enantiomer-Selective Acylation with Flurous Phase Labeling: A New Method for the Resolution of Racemic Alcohols, J. Org. Chem., (2002), vol. 67, pp. 1781-1785.
Kunz Horst et al., Das System 2-Halogenethylester/Cholinester als Zweistufen-Schuutzgruppe fur die Carboxylfunktion von Aminosauren und Peptiden, Chem. Ber., (1979), vol. 112, pp. 2145-2157.
Larock Richard C., Comprehensive Organic Transformations: A Guide To Functional Group Preparations—Acid Halides to Acid Anhydrides.

(Continued)

*Primary Examiner*—Kamal A. Saeed
*Assistant Examiner*—Susannah L. Chung
(74) *Attorney, Agent, or Firm*—Barbara E. Kurys

(57) ABSTRACT

A process is described for preparing chiral, nonracemic, cis-configured 1,3-disubstituted cyclohexanols of the formula (I)

(I)

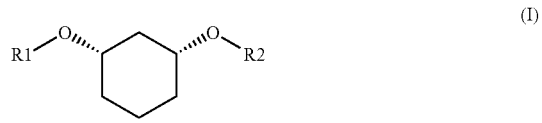

where the radicals are as defined, by means of enzymatic optical resolution.

28 Claims, No Drawings

OTHER PUBLICATIONS

Larock Richard C., Comprehensive Organic Transformations: A Guide To Functional Group Preparations—Halogenations Of Alcohols.

Larock Richard C., Comprehensive Organic Transformations: A Guide to Functional Group Preparations—Halogenations Of Hydrocarbons.

Mattson Anders et al., Kinetic Resolution of Chiral Auxiliaries with C2-Symmetry by Lipase-Catalyzed Alcoholysis and Aminolysis, Acta Chemica Scandinavica, (1996), vol. 50, pp. 918-921.

Perkin William Henry et al., An Investigation Of The Action Of Halogens on 2:4-Dimenthylbenzoyl Chloride.

Schelhaas Michael et al., Enzymatische Synthese von Peptiden und Ras-Lipopeptiden unter Verwendung des Cholinesters als Ioslichkeitsvermittelnder Schutz und Aktivierungsgruppe, Agnew. Chem., (1996), pp. 82-85.

Suemune Hiroshi et al., Enantioselective Synthesis of (1S, 3S, 5R)-1-Acetoxy-5-benzyl-oxycyclohexan-3-ol and Its Application to the Synthesis of Compactin Lactone Moiety and Quinic Acid, Tetrahedron Asymmetry, (1992), vol. 3, No. 2, pp. 297-306.

Wirz Beat et al., Multiselective enzymatic reactions for the synthesis of protected homochiral cis-and trans-1,3,5-cyclohexanetriols, Tetrahedron: Symmetry, (2000), vol. 11, pp. 4171-4178.

Yamano Toru et al., A Practical Method for Optical Resolution of Racemic Alcohols or Esters via Lipase-Catalyzed Transformation and Sulfation, Chemistry Letters, (2000), pp. 448-449.

Zhao Yurui et al., Asymmetrization of all-cis-3,5-dihydroxy-1-(methoxycarbonyl)cyciohexane and of the 4-methyl and 4-ethyl substituted homologues, Tetrahedron: Asymmetry, (2000), vol. 11, pp. 3887-3900.

Die Delepine-Reaktion bei 2-Aryl-4-chlormethyl-oxazolen.

* cited by examiner

PROCESS FOR PREPARING THE ENANTIOMERIC FORMS OF CIS-CONFIGURED 1,3-CYCLOHEXANEDIOL DERIVATIVES

DESCRIPTION

The invention relates to a process for preparing chiral, nonracemic, cis-configured 1,3-disubstituted cyclohexanols of the formula (I)

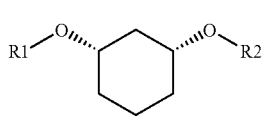

(I)

Variously substituted, cis-configured 1,3-disubstituted cyclohexane derivatives (compounds of the formula (I) where $R^1 \neq R^2$) are central building blocks or precursors of the active pharmaceutical ingredients which are described in WO 03/020,269 and are generally suitable for treating lipid metabolism disorders, type II diabetes and syndrome X, inter alia.

The syntheses which are described in the patent application Ser. No. 03/020,269 of the nonracemic, cis-configured 1,3-cyclohexane derivatives cannot be considered as industrial processes: for example, alkylations with NaH/DMF on the multi-kg scale cannot be carried out safely (C&EN, Sep. 13, 1982, 5). Moreover, the alkylation by the Bu$_2$SnO method on the industrial scale entails unacceptably high cost and inconvenience; the removal of the tin compounds from the desired products is very difficult and usually incomplete even when chromatographic separating methods are used. The disposal of the tin compounds is a further problem and a cost factor. The separation of the enantiomers (optical resolution) by chromatography on a chiral phase is likewise inconvenient and too expensive. In addition, it is necessary for chromatographic enantiomer resolution that the racemic compound is present in good chemical purity, which can be achieved in many cases by additional, preceding chromatography.

Other methods which have been described in literature for synthesizing cis-1,3-cyclohexanediol building blocks or derivatives, for example the opening of epoxycyclohexanes (P. Crotti, V. Di Bussolo, L. Favero, M. Pineschi, F. Marianucci, G. Renzi, G. Amici, G. Roselli, Tetrahedron 2000, 56, 7513–7524 and cit. lit.) or the metallized-catalyzed hydroboration of cyclohexene derivatives (J. A. Brinkmann, T. T. Nguyen, J. R. Sowa, Jr., Org. Lett. 2000, 2, 981–983; C. E. Garrett, G. C. Fu, J. Org. Chem. 1998, 63, 1370–1371) are predominantly unsatisfactory with regard to the regioselectivity and the stereoselectivity. The total number of stages is additionally distinctly higher. They cannot be considered as industrial processes.

The synthesis of cis-1,3-cyclohexanediol derivatives starting from cis,cis-1,3,5-cyclohexanetriol or cis,cis-1,3,5-cyclohexanetriol derivatives (L. Dumortier, M. Carda, J. Van der Eycken, G. Snatzke, M. Vandewalle, Tetrahedron: Asymmetry 1991, 2, 789–792; H. Suemune, K. Matsuno, M. Uchida, K. Sakai, Tetrahedron: Asymmetry 1992, 3, 297–306) are likewise very complicated and uneconomic as a consequence of the high number of stages and therefore unsuitable for industrial use. The enzymatic reaction of the cis/trans mixture of 1,3-cyclohexanediol with S-ethyl thiooctanoate cannot be considered as an industrial process. Apart from the odor nuisance which can barely be avoided when working with the sulfur compounds and the fact that to achieve the required conversion, the ethanethiol which is released has to be removed continuously, the reaction described leads to a mixture of 9 isomeric forms or derivatives of cyclohexanediol, i.e. the unconverted isomers (S,S)-diol, (R,R)-diol and (R,S)-diol, also the monoacylated products (S,S)-monooctanoate, (R,R)-monooctanoate and (R,S)-monooctanoate, and thirdly the group of the diacylated products (S,S)-dioctanoate, (R,R)-dioctanoate and (R,S)-dioctanoate. The optically active, monoacylated, cis-configured (R,S)-monooctanoate takes up only a proportion of about 12% in the fraction of the monoacylated cyclohexanediols. A preparation and isolation of this product on the preparative scale has not been described, but in view of the ratios of amounts and the separating problem outlined, cannot be economic. In addition, it is known that partially acylated di- or polyhydroxy compounds tend to acyl group migrations. When this occurs, for example, in the course of the purification of the (R,S)-monooctanoate (for example in the chromatography on silica gel or in aqueous extraction) or in the course of a subsequent reaction (for example during the alkylation of the free hydroxyl group), this leads to a distinct reduction in the optical purity or to racemization.

The cis-configured (R,S)-diols and the diacylated (R,S)-compounds are not optically active and therefore not of interest.

It is therefore an object of the present invention to develop a process which does not have the disadvantages mentioned.

The present invention provides a process for preparing a chiral, nonracemic compound of the formula I

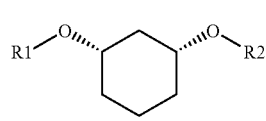

(I)

where:
$R^1$ is

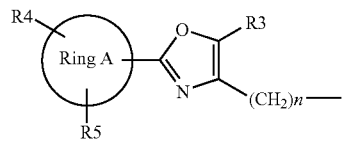

where:
ring A is phenyl, 5–12 membered heteroaromatic ring which may contain from one to four heteroatoms from the group of N, O and S, 8 to 14 membered aromatic ring, $(C_3-C_8)$-cycloalkyl;
$R^3$ is H, F, Cl, Br, OH, $NO_2$, $CF_3$, $OCF_3$, $(C_1-C_6)$-alkyl, $(C_3-C_8)$-cycloalkyl, phenyl;
$R^4$, $R^5$ are H, F, Cl, Br, OH, $NO_2$, $CF_3$, $OCF_3$, $OCF_2H$, $OCF_2-CF_3$, $OCF_2-CHF_2$, $SCF_3$, O-phenyl, $(C_1-C_6)$-alkyl, O—$(C_1-C_6)$-alkyl, O—$(C_1-C_6)$-alkyl-O—$(C_1-C_3)$-alkyl;
n is from 1 to 3;

and
$R^2$ is $(C_1-C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—$O(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, NH—CO—C$(CH_3)_3$, hydroxyl, $OCF_3$, O—$(C_1-C_6)$-alkyl, COOH, CO-benzoxy, CO—$O(C_1-C_6)$-alkyl, $(C_1-C_6)$-alkyl, O—$(C_1-C_6)$-alkyl or tetrazole, or;

$R^2$ is an OH protecting group (PG), for example benzyloxymethyl, benzyl, para-methoxybenzyl or tert-butyldimethylsilyl;

which comprises
A)
a) alkylation (alk-$R^2$/alk-PG)

reacting cis-1,3-cyclohexanediol of the formula (II)

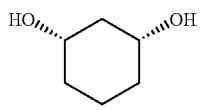
(II)

with a compound of the formula (III)

$X^1—R^2$ (III)

where $R^2$ is as defined above and
$X^1$ is Cl, Br, I, OMs (O-mesyl), OTs (O-tosyl), OTf (O-triflate);

in the presence of bases in a suitable solvent to give a racemic compound of the formula (IV)

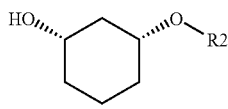
(IV)

where $R^2$ is as defined above;
b1) enzymatic ester formation (EF)+separation (S)

subjecting the resulting compounds of the formula (IV) to stereoselective enzymatic ester formation (EF), in which the alcohols are admixed with an acyl donor, for example a vinyl ester $R^6$—O—CH=$CH_2$ or an acid anhydride $R^6$—O—$R^6$, where $R^6$ is as defined above, and the enzyme in an organic solvents, for example dichloromethane, and the resulting mixture is stirred at −20 to 80° C. and, after the reaction has ended, one stereoisomer is present as an ester of the formula (V)

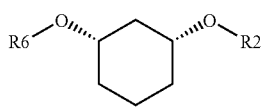
(V)

where
$R^6$ is C(=O)—$(C_1-C_{16})$-alkyl, C(=O)—$(C_2-C_{16})$-alkenyl, C(=O)—$(C_3-C_{16})$-alkynyl, C(=O)—$(C_3-C_{16})$-cycloalkyl, where one or more carbon atoms may be replaced by oxygen atoms and be substituted by 1–3 substituents from the group of F, Cl, Br, $CF_3$, CN, $NO_2$, hydroxyl, methoxy, ethoxy, phenyl and CO—$O(C_1-C_4)$-alkyl, CO—$O(C_2-C_4)$-alkenyl, which may in turn be substituted by 1–3 substituents from the group of F, Cl, Br, $CF_3$, and $R^2$ is as defined above, and the other stereoisomer is present unchanged as the alcohol of the formula (IV), and are therefore separated from each other by utilizing their different chemical or physicochemical properties (for example $R_f$ values or solubility differences in water or other solvents) (separation S), for example by simple chromatography on silica gel, by extraction (for example heptane/methanol or org. solvent/water) or else by a further subsequent chemical reaction, for example of the alcohol, in which the ester does not take part, or b2) enzymatic ester hydrolysis [=chemical esterification (CE)+enzymatic hydrolysis (EH)]+separation (S)

subjecting the resulting compounds of the formula (IV) to a stereoselective enzymatic ester hydrolysis, in which the racemic alcohol is initially converted by chemical esterification (CE), for example by means of acid chlorides $R^6$—Cl or acid anhydrides $R^6$—O—$R^6$, in the presence of bases, for example triethylamine, to the racemic ester of the formula (V)

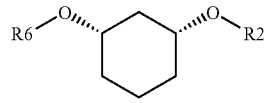
(V)

where $R^6$ and $R^2$ are each as defined above, which, to carry out the stereoselective enzymatic ester hydrolysis (EH), is then taken up in homogeneous or heterogeneous, aqueous, aqueous-organic or organic media, and reacted, in the presence of an enzyme in the case of hydrolysis with water and in the case of alcoholysis with an alcohol, for example n-butanol, at a temperature of 10–80° C., and after the reaction has ended, one stereoisomer is present as the alcohol of the formula (IV) and the other is present unchanged as the ester of the formula (V) and can thus be separated from each other as described under b1), and the enantiomer of the formula (IV) occurring as an alcohol is further processed as described under d), or
c) Chemical Hydrolysis (CH)

hydrolyzing the enantiomer of the formula (V) occurring as an ester to the chemically enantiomeric alcohol by known methods and
d) Alkylation (alk-$R^1$)

reacting further with a compound of the formula (VI)

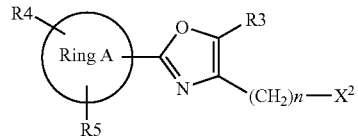
(VI)

where ring A, $R^3$, $R^4$, $R^5$ and n are each as defined above and $X^2$ is Cl, Br, I, OTs, OMs, OTf;

in the presence of bases in a suitable solvent to give the compound of the formula (I), and e) Detachment of the Protecting Group PG (detPG)

if $R^2$ is an OH protecting group (PG) as defined above and $R^2$, converting the compound of the formula (Ia)

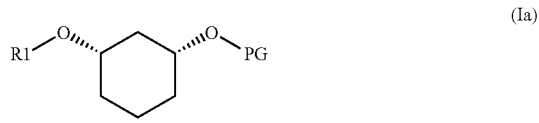

(Ia)

where $R^1$ and PG are each as defined above, by detaching the protecting group by known methods, for example detachment of PG=benzyloxymethyl or PG=benzyl by hydrogenating over Pd/C, or detachment of PG=para-methoxybenzyl with, for example DDQ (2,3-dichloro-5,6-dicyanobenzoquinone), or detachment of PG=tert-butyldimethylsilyl, for example with $Bu_4NF$, to a compound of the formula (VII)

(VII)

where $R^1$ is as defined above, f) Alkylation (alk-$R^2$)

then reacting it with a compound of the formula (III)

$$X^1-R^2 \quad (III)$$

where $X^1$ and $R^2$ are each as defined above, in the presence of bases in a suitable solvent to give a compound of the formula (I), the product or the enantiomeric form, it being also possible to change the sequence of individual reaction steps as described above under A):

A)     alk-$R^2$→EF+S/CE+EH+S[→CH]→alk-$R^1$ [→DetPG→alk-$R^2$]→product/enantiomeric form to:

B)     alk-$R^1$→EF+S/CE+EH+S[→CH]→alk-$R^2$ [→DetPG→alk-$R^2$]→product/enantiomeric form or C)     alk-PG→EF+S/CE+EH+S→CH→alk-$R^2$→DetPG→alk-$R^1$→product/enantiomeric form or D)     alk-PG→EF+S/CE+EH+S→alk-$R^1$→DetPG→alk-$R^2$→product/enantiomeric form.

Possible process variants are illustrated hereinbelow in Schemes I to IV:

SCHEME I

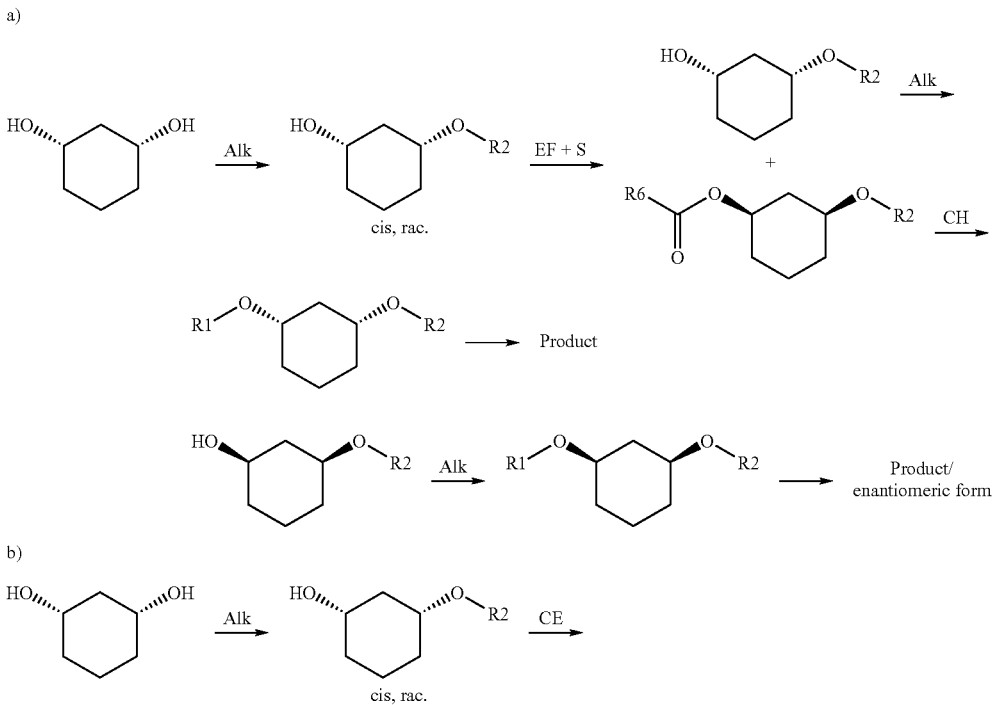

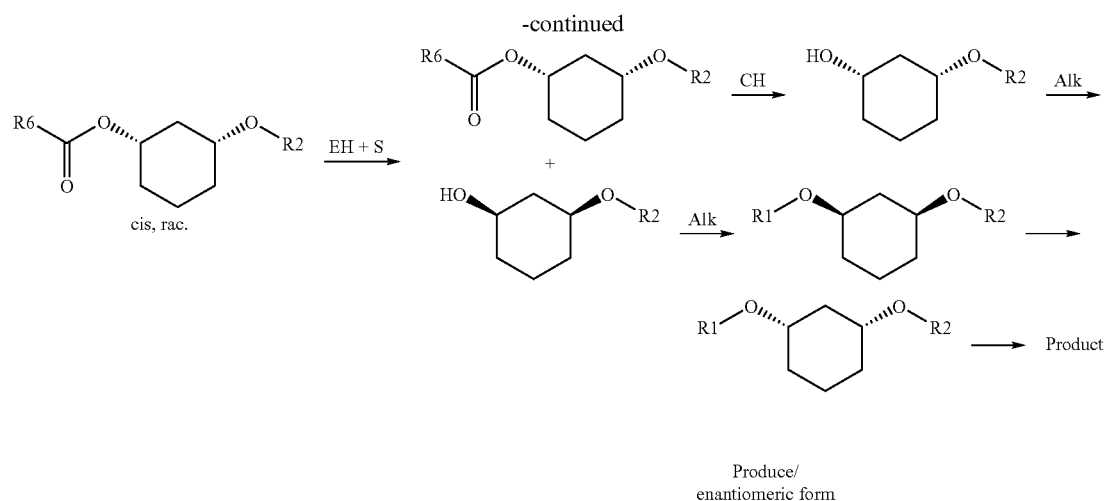
SCHEME II
a)
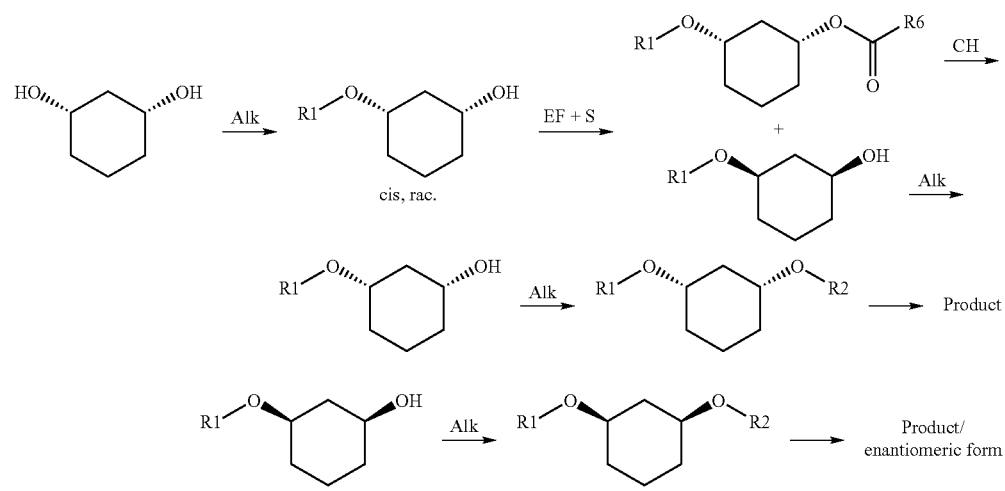
b)
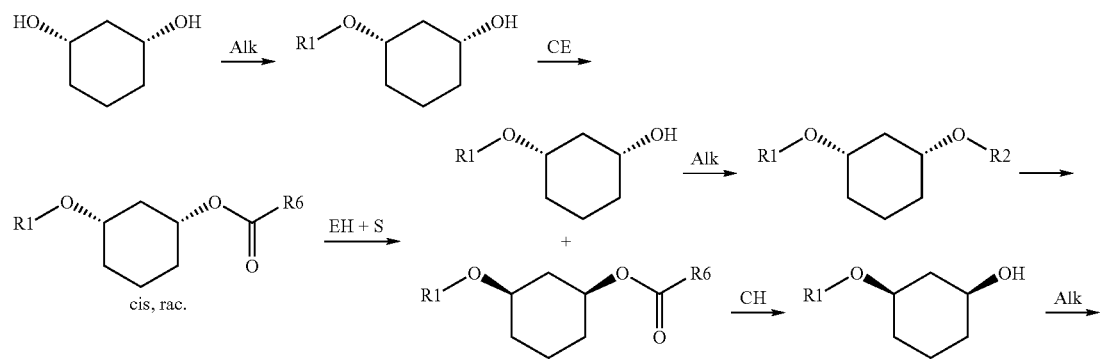

-continued
Product
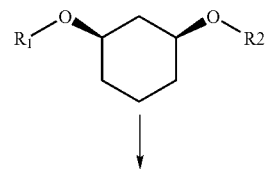
Produce/
enantiomeric form
SCHEME III
a)
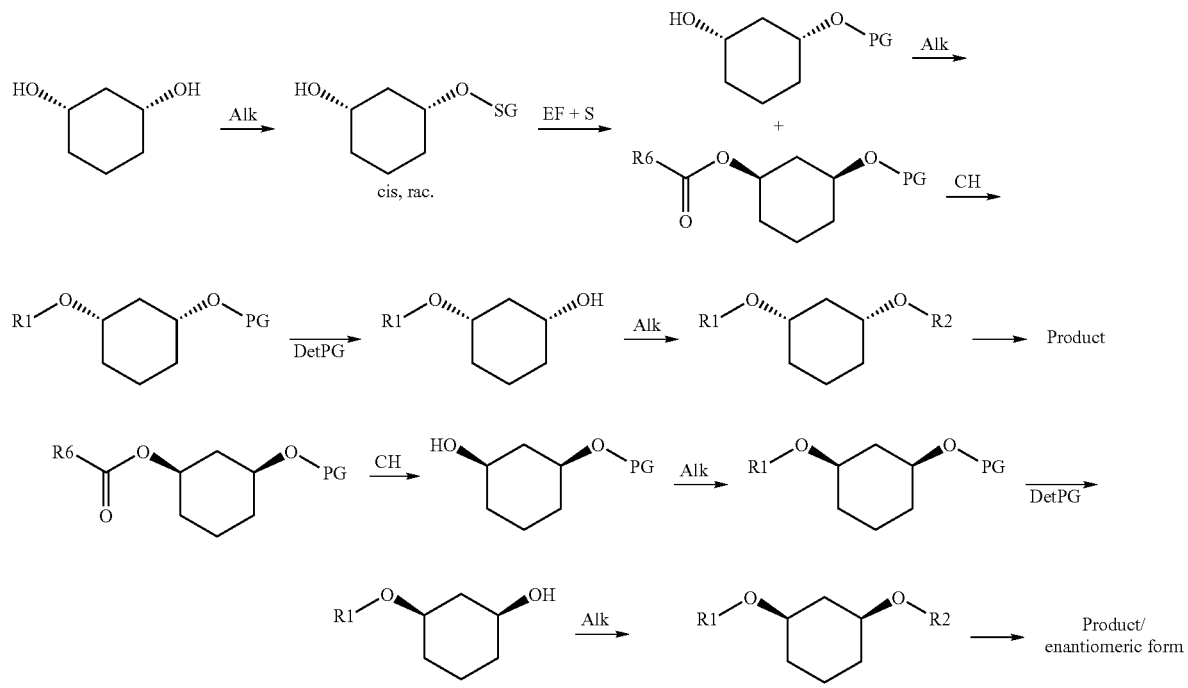
SCHEME III
b)
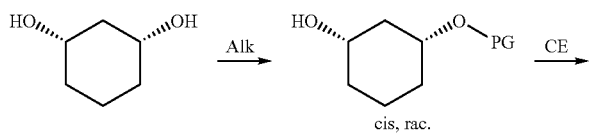

-continued
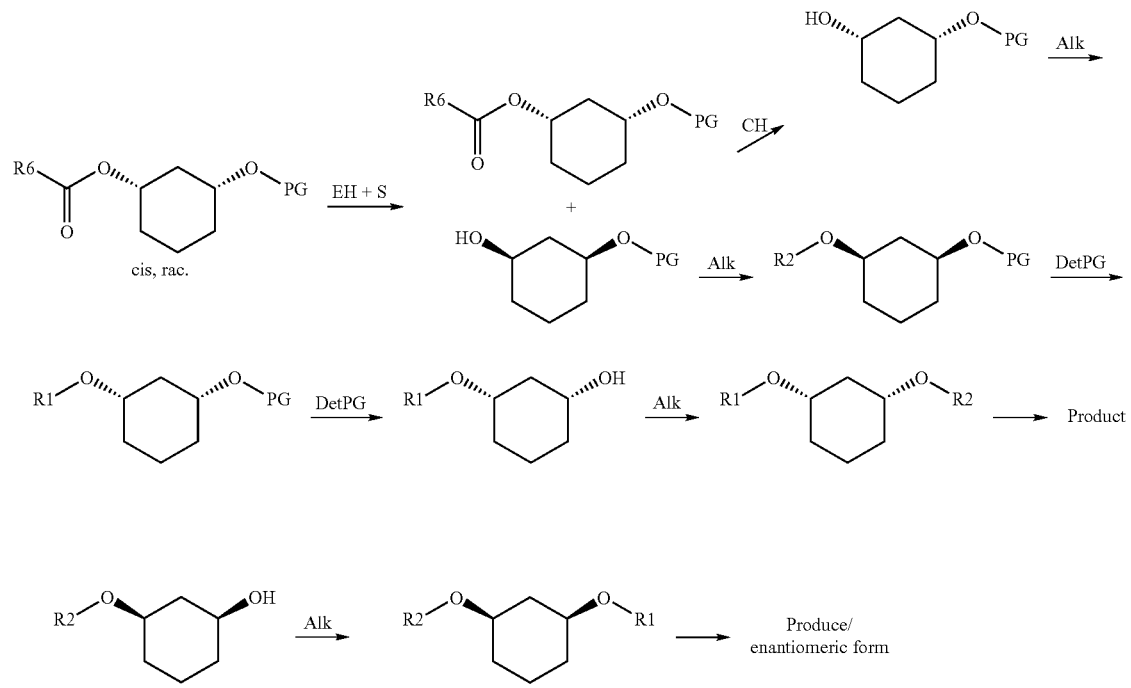
SCHEME IV
a)
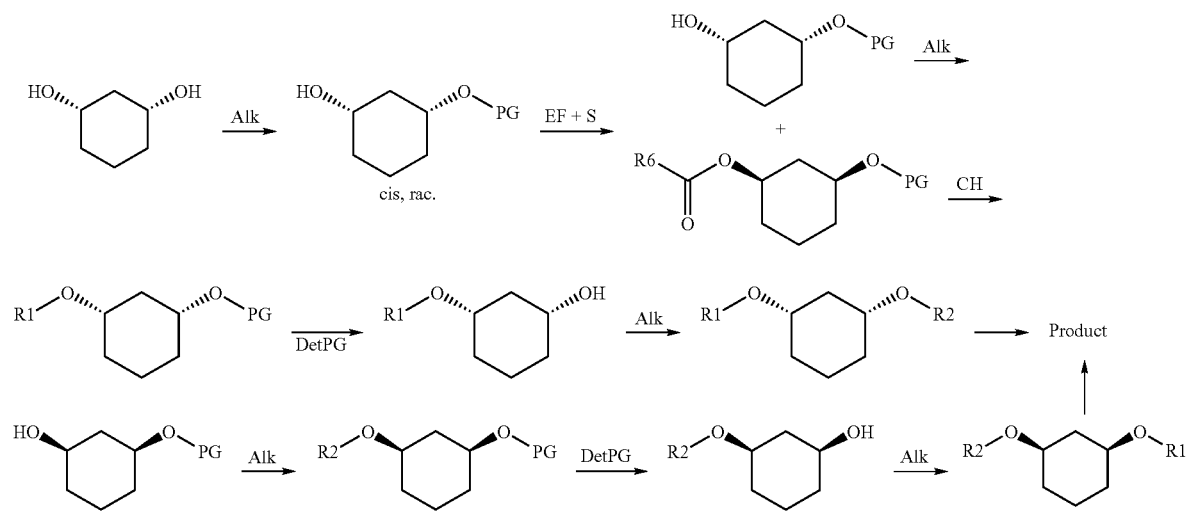
SCHEME IV
b)
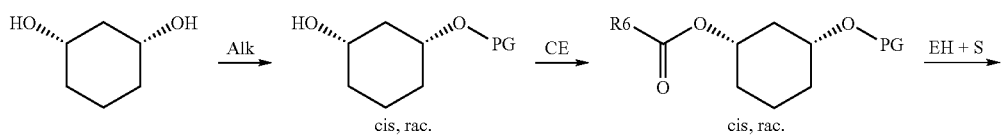

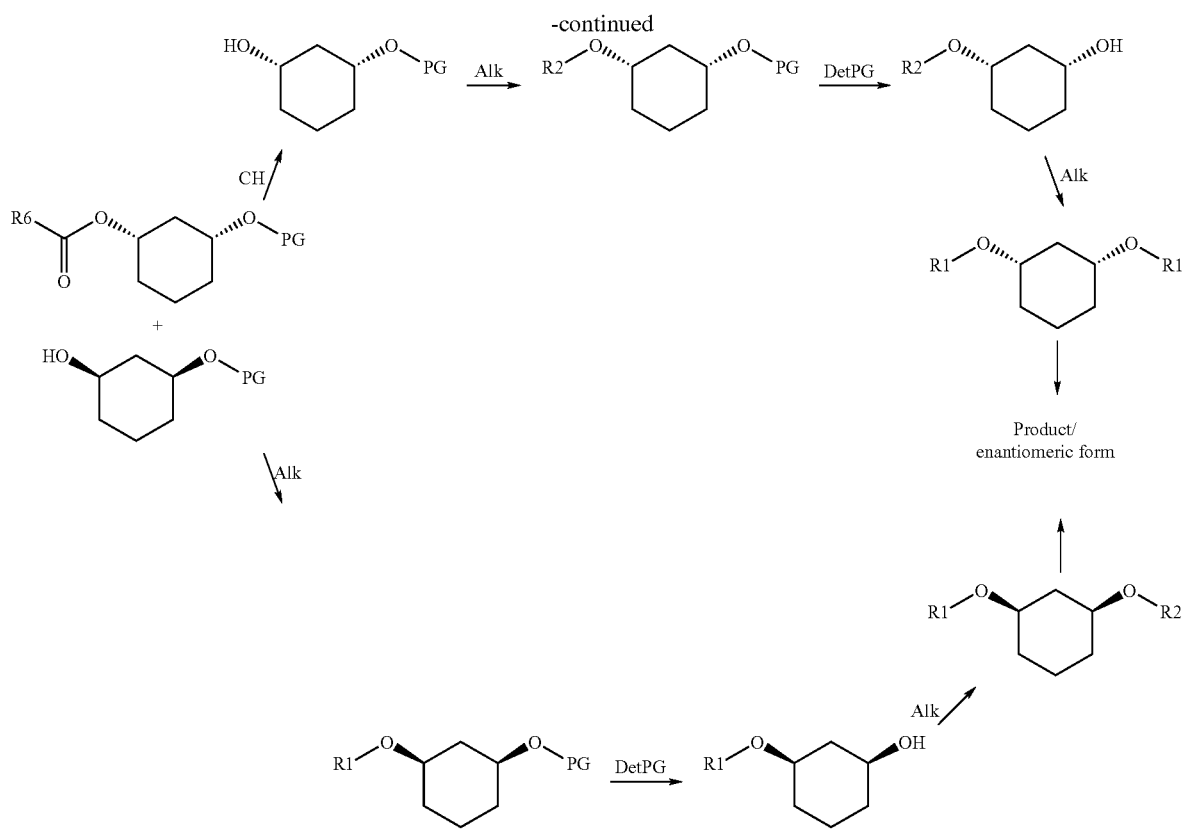

The process according to the invention is economic, simple and rapid. The process completely eliminates the risk of acyl group migration, does not require equimolar amounts of optically pure starting materials or auxiliaries, any expensive reagents, any optical resolution by chromatography on chiral phases, any disproportionately large amounts of solvent or any cost-intensive working steps.

The loss of 50% which is typical for optical resolutions can be avoided by using both enantiomers and changing the sequence of the alkylations. Preference is given to what is known as the enantioconvergent method (see Scheme IV or Method C and D)) in which the procedure is, for example, as follows: alkylation of cis-1,3-cyclohexanediol of the formula (II) with a compound of the formula (III) with a PG selected as $R^2$ such that PG can be detached again simply and selectively in the course of the further synthesis, and PG is thus, for example, benzyl, or para-methoxybenzyl or tert-butyldimethylsilyl, subjecting the resulting compound of the formula (IV) to stereoselective enzymatic ester formation or ester hydrolysis (see above) and, after completion of separation of unconverted alcohol and ester, converting them separately and by different routes to the same optically pure product by reacting the alcohol (as described in the first part), for example, with a compound of the formula (VI) to give a compound of the formula (Ia), then converting it by detaching the PG group to give a compound of the formula (VII), and then reacting it with a compound of the formula (III) where $R^2$ is as desired in the product to give a compound of the formula (I), and converting the isomeric ester by simple ester hydrolysis to a compound of the formula (IV), and then reacting with a compound of the formula (III) where $R^2$ is as desired in the product to give a compound of the formula (VIII)

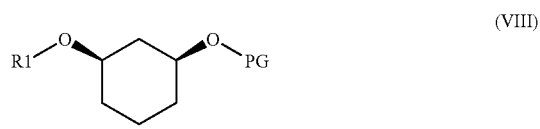

(VIII)

then converting it by detaching the PG group to give a compound of the formula (IV)

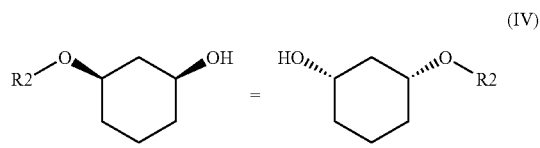

(IV)

and then reacting it with a compound of the formula (VI) to give a compound of the formula (I).

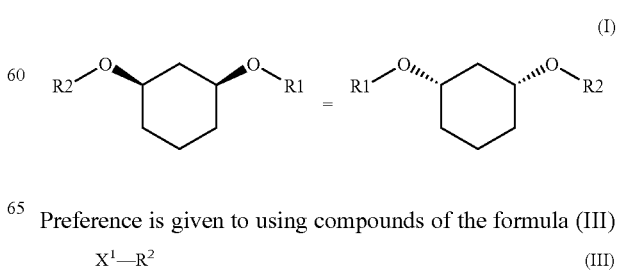

(I)

Preference is given to using compounds of the formula (III)

$X^1\text{—}R^2$ (III)

where
X¹ is Cl, Br, I, OMs or OTs, particular preference to using those where
X¹ is Cl, Br or I.

Preference is given to a process for preparing the compounds of the formula (I)

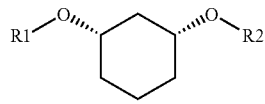
(I)

where
R¹ is
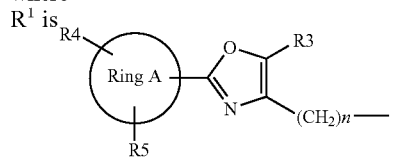

where
ring A is phenyl, 5–12 membered heteroaromatic ring which may contain one or more heteroatoms from the group of N, O and S, fused/bicyclic 8 to 14 membered aromatic ring, $(C_3–C_8)$-cycloalkyl;
$R^3$ is H, $CF_3$, $(C_1–C_6)$-alkyl, $(C_3–C_8)$-cycloalkyl, phenyl;
$R^4$, $R^5$ are H, F, Br, $CF_3$, $OCF_3$, $(C_1–C_6)$-alkyl, $O—(C_1–C_6)$-alkyl;
n is from 1 to 2;
$R^2$ is $(C_1–C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—C$(CH_3)_3$, hydroxyl, $OCF_3$, $O—(C_1–C_6)$-alkyl, COOH, CO-benzoxy, $CO—O(C_1–C_6)$-alkyl, tetrazole, thiazolidin-2,4-dione, indole and $(C_6–C_{10})$-aryl, were thiazolidin-2,4-dione and aryl in turn maybe substituted by F, Cl, Br, $CF_3$, CN, $NO_2$, NHAc, NHTs, NHBoc, NHCbz, NH—CO—C$(CH_3)_3$, hydroxyl, $OCF_3$, $O—(C_1–C_6)$-alkyl, COOH, CO-benzoxy, $CO—O(C_1–C_6)$-alkyl, $(C_1–C_6)$-alkyl, $O—(C_1–C_6)$-alkyl or tetrazole.

Particular preference is given to a process for preparing the compounds of the formula (I)

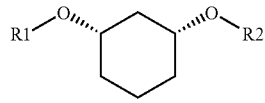
(I)

where:
R¹ is
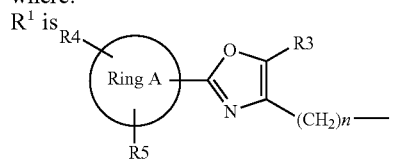

where
ring A is phenyl;
$R^3$ is $(C_1–C_4)$-alkyl;
$R^4$, $R^5$ are H, $(C_1–C_4)$-alkyl, $O—(C_1–C_4)$-alkyl;
n is 1;
$R^2$ is $(C_1–C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—C$(CH_3)_3$, hydroxyl, $OCF_3$, $O—(C_1–C_6)$-alkyl, COOH, CO-benzoxy, $CO—O(C_1–C_6)$-alkyl, tetrazole, thiazolidin-2,4-dione, indole and $(C_6–C_{10})$-aryl, were thiazolidin-2,4-dione and aryl in turn maybe substituted by F, Cl, Br, $CF_3$, CN, $NO_2$, NHAc, NHTs, NHBoc, NHCbz, NH—CO—C$(CH_3)_3$, hydroxyl, $OCF_3$, $O—(C_1–C_6)$-alkyl, COOH, CO-benzoxy, $CO—O(C_1–C_6)$-alkyl, $(C_1–C_6)$-alkyl, $O—(C_1–C_6)$-alkyl or tetrazole.

The alkyl radicals in the substituents $R^2$, $R^3$, $R^4$ and $R^5$ may be either straight-chain or branched.

In this context, a heteroaromatic ring refers to both mono- and bicyclic rings having a maximum of 4 heteroatoms, in particular those which contain up to 4 nitrogen atoms and/or 1 oxygen or 1 sulfur atom, for example furan, thiophene, thiazole, oxazole, thiadiazole, triazole, pyridine, triazine, quinoline, isoquinoline, indole, benzothiophene, benzofuran, benzotriazole.

Aromatic rings may be mono- or bicyclic and also be fused, for example naphthyl, benzo[1,3]dioxole, dihydrobenzo[1,4]dioxin.

The racemic, cis-configured 1,3-cyclohexane derivatives of the formula (IV) and of the formula (VII) are prepared by monoalkylating cis-cyclohexanediol (compound of the formula II), but can also be prepared by reductively opening appropriate acetals (R. Hunter et al., *J. Org. Chem.* 1993, 85, 6756), and also by reductive ether formation starting from silyl ethers and aldehydes or ketones (J. S. Bajwa, X. Jiang, J. Slade, K. Prasad, O. Repic, T. J. Blacklock, *Tetrahedron Lett.* 2002, 43, 6709–6713).

The alkylating reagents of the formula III are commercially obtainable or can be prepared by literature methods, for example by free-radical side chain halogenation (see literature review by R. C. Larock, Comprehensive Organic Transformations, p. 313, 1989 VCH Publishers, Inc.) or from the alcohols or derivatives preparable therefrom (see literature review by R. C. Larock, Comprehensive Organic Transformations, p. 353–363, 1989 VCH Publishers, Inc.).

Also known (see *J. Chem. Soc.* 1925, 127, 2275–2297; *J. Chem. Soc.* 1922, 121, 2202–2215) is the preparation of various 2-bromomethylbenzoyl bromides by free-radical bromination, which may then be converted by further reaction with alcohols to the bromomethylbenzoic esters belonging to the group of the alkylating reagents of the formula III.

The alkylating reagents of the formula (VI) or the alcohols $X^2$=OH which can serve as precursors are commercially obtainable or can be prepared by literature methods [a]. The Chemistry of Heterocyclic Compounds (Ed.: A. Weissberger, E. C. Taylor): Oxazoles (Ed.: I. J. Turchi); b) Methoden der Organischen Chemie, Houben-Weyl, 4th edition, Hetarene III, subvolume 1; c) I. Simit, E. Chindris, *Arch. Pharm.* 1971, 304, 425; d) Y. Goto, M. Yamazaki, M. Hamana, *Chem. Pharm. Bull.* 1971, 19 (10), 2050–2057].

The alkylating reagents of the formula III and VI are reacted with 1,3-cyclohexanediol or 1,3-cyclohexanediol derivatives in the presence of bases. Suitable bases are, for example, hydroxides such as KOH, carbonates such as $Cs_2CO_3$, alkoxides such as KOtBu and also compounds such as LDA, BuLi, LiHMDS, KH, NaH and NaHMDS. Suitable solvents are, for example, THF, MTBE, DME, NMP, DMF and chlorobenzene.

For optical resolution of the alcohols, they are taken up in organic solvents, for example dimethoxyethane (DME), methyl tert-butyl ether (MTBE), diisopropyl ether (DIPE), THF, n-hexane, cyclohexane, toluene, chlorobenzene, acetone, dimethylformamide (DMF), dichloromethane, 1,2-dichloroethane and tert-butanol, acyl donors such as vinyl acetate, vinyl propionate, vinyl butyrate, 2,2,2-trifluoroethyl 2H,2H-perfluorodecanoate, ethoxyvinyl acetate, p-nitro- or p-chlorophenyl acetate, oxime esters, acetic anhydride, propionic anhydride, succinic anhydride, glutaric anhydride, isovaleric anhydride, 2,2,2-trichloroethyl butyrate, 2,2,2-trifluoroethyl 2H,2H-perfluorodecanoate are added and the reaction mixture is subsequently admixed with a suitable enzyme and stirred at from −20 to 80° C. The proportion of cosolvent in the solution is preferably 10–90%, but it is in some cases also advantageous to carry out the enzymatic reaction in pure acyl donor, for example vinyl acetate, without cosolvent.

For optical resolution of the ester derivatives, for example acetyl-, propionyl-, butyryl- or glutaryl-, they are subjected in homogeneous or heterogeneous, aqueous, aqueous-organic or organic media, in the presence of a suitable enzyme, to stereoselective hydrolysis or alcoholysis (for example with n-butanol) at a temperature of 10–80° C., optionally in the presence of cosolvents (see above) and of a buffer, the reaction mixture preferably containing 2–50% by weight of ester.

The abovementioned ester derivatives can be prepared by literature methods, for example by reacting the alcohol with acid chlorides such as acetyl chloride or anhydrides such as acetic anhydride, in the presence of an amine, for example triethylamine or pyridine (see literature review by R. C. Larock, Comprehensive Organic Transformations, p. 978, 1989 VCH Publishers, Inc.).

When the reaction has ended, the products or the enantiomers can be separated in a simple manner, for example by extraction by literature methods [a]. T. Yamano, F. Kikumoto, S. Yamamoto, K. Miwa, M. Kawada, T. Ito, T. Ikemoto, K. Tomimatsu, Y. Mizuno, Chem. Lett. 2000, 448; b). B. Hungerhoff, H. Sonnenschein, F. Theil, J. Org. Chem. 2002, 67, 1781] or by employing chromatographic methods.

A further method is, on completion of the enzymatic reaction, to distinctly increase the water solubility of the remaining alcohol by derivatization, for example by acylation with cyclic anhydrides, e.g. with glutaric anhydride, or by conversion to a cholin ester [a]. H. Kunz, M. Buchholz, Chem. Ber. 1979, 112, 2145; b). M. Schelhaas, S. Glomsda, M. Hänsler, H.-D. Jakubke, H. Waldmann, Angew. Chem. 1996, 108, 82] and thus to achieve separation from the water-insoluble or sparingly water-soluble esters by extraction. After the separation, the derivatization of the alcohols can be reversed by chemical or enzymatic hydrolysis.

A particularly interesting means for separating the enantiomers in the case of the enzymatic acylation is to select the acyl donor in such a way that the acylated enantiomer is distinctly more water-soluble than the unconverted alcohol. Suitable acyl donors are, for example, cyclic anhydrides such as succinic anhydride. On completion of the enzymatic acylation, the acylation product bears a free carboxyl group which enables rapid removal of the product by aqueous extraction under basic conditions, for example with sat. aqueous $NaHCO_3$ solution.

In enzymatic optical resolution by ester hydrolysis, the procedure is preferably to admix an ester of the formula (I), for example where $R^1$=$COCH_3$, $COCH_2CH_3$ or $COCH_2CH_2CH_2COOH$ in an aqueous or alcoholic solution, with an esterase or lipase and stirred. It may be advantageous to buffer the solution mentioned, for example with phosphate or TRIS [=tris(hydroxymethyl)methylamine] buffer. The additive may, for example, be 0.01–1.0 molar. A favorable buffer range is pH 5–10.

The enzymes used are preferably hydrolases from mammalian livers, for example lipase from porcine pancreas (fluka), or from microorganisms, for example Lipase B from Candida antarctica (Roche Diagnostics), Lipase OF from *Candida rugosa* (Meito Sangyo), Lipase SL from *Pseudomonas cepacia* (Meito Sangyo), Lipase L-10 from *Alcaligenes* spec. (Roche Diagnostics), and Lipase QL from *Alcaligenes* spec. (Meito Sangyo). When the esters used are glutaric acid derivatives, for example mono-(3-benzyloxy-cyclohexyl) glutarate, it may be advantageous, instead of the abovementioned lipases, to use glutaryl-7-ACA Acylase (Roche Diagnostics).

Particular preference is given to using Lipase B from *Candida antarctica* (Roche Diagnostics), and it may be advantageous to use the free enzyme or an immobilized form of the enzyme, for example one of the three products which are currently obtainable commercially.

Each of the enzymes mentioned can be used in free or in immobilized form (Immobilized Biocatalysts, W. Hartmeier, Springer Verlag Berlin, 1988). The amount of enzyme is selected freely depending on the reaction rate or on the desired reaction time and on the type of the enzyme (for example free or immobilized) and can be determined easily by simple preliminary experiments. The enzyme can be recovered by freeze-drying. The removal (and optional later reuse) of the enzyme can be eased by immobilization.

Suitable reaction control always succeeds in obtaining at least one enantiomer in optically pure form. When optically pure ester is desired, the conversion in the case of an enzymatic ester formation should be less than (or equal to) 50%, or in the case of an enzymatic hydrolysis or alcoholysis, greater than (or equal to) 50%. When optically pure alcohol is desired, the conversion in the case of enzyme-catalyzed ester formation should be greater than (or equal to) 50%, or in the case of hydrolysis or alcoholysis, less than (or equal to) 50%.

The conversion of the enzymatic reaction was determined either by HPLC directly from the reaction mixture or by calculation from the optical purities of the reaction products (ester and acid) which were likewise determined directly from the reaction mixture by HPLC on a chiral phase.

The citation of any reference herein should not be construed as an admission that such reference is available as "Prior Art" to the instant application.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

The examples which follow are intended to illustrate the present invention in detail.

EXAMPLES

All isolated products and crude product mixtures were identified by $^1H$ NMR and mass spectra or by HPLC.

The optical purity of the esters and alcohols was determined by HPLC, for example on Chiralpak AD 250×4.6 (Daicel) or Chiracel OD 250×4.6.

Scheme Ia:

Example 1

Synthesis of Racemic Methyl cis-2-(3-hydroxycyclohexyloxymethyl)-6-methylbenzoate

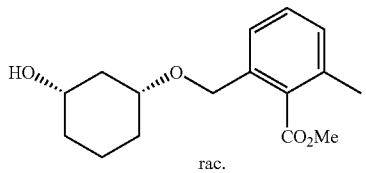

500 g (4.3 mol) of cis-1,3-cyclohexanediol were dissolved in 5 l of NMP and admixed with 336 g (3.0 mol) of potassium tert-butoxide (KOtBu). The internal temperature rose to 28° C. The mixture was stirred for 30 min, then cooled to –5° C. and admixed dropwise with 370 g (approx. 94%, approx. 1.4 mol) of methyl 2-bromomethyl-6-methylbenzoate which may be prepared, for example, by methanolyzing 2-bromomethyl-6-methylbenzoyl bromide or by brominating methyl 2,6-dimethylbenzoate. The mixture was stirred for 30 min and then diluted with 5 l of water. After washing three times with 3 l of n-heptane each time and discarding the n-heptane solutions, the remaining aqueous phase was extracted four times with 2.5 l of MTBE each time. The combined MTBE phases were washed once with 5 l of water, dried over $Na_2SO_4$ and subsequently concentrated by evaporation under reduced pressure. 234 g of the desired compound were obtained as a yellowish oil and were used in the next reaction (for example an optical resolution) without further purification; $^1$H NMR ($CDCl_3$), δ =1.27 (m, 1H), 1.45 (m, 1H), 1.55 (m, 1H), 1.74 (m, 1H), 1.83 (m, 1H), 2.05 (m, 1H), 2.34 (s, 3H), 3.47 (m, 1H), 3.72 (m, 1H), 3.91 (s, 3H), 4.58 (dd, 2H), 7.15 (d, 1H), 7.20 (d, 2H), 7.27 (m, 1H).

Example 2

Optical Resolution of Methyl cis-2-(3-hydroxycyclohexyloxymethyl)-6-methylbenzoate

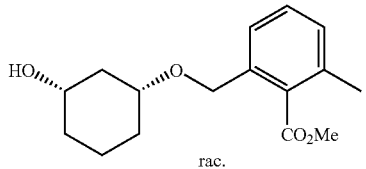

490 g of the crude, racemic methyl cis-2-(3-hydroxycyclohexyloxymethyl)-6-methylbenzoate (see Example 1) were dissolved in 3.1 l of methylene chloride and 850 ml of vinyl acetate, admixed with 18 g of Novozym 435 and stirred at 21–24° C. After 28 h, a further 2 g of Novozym 435 were added. After a total of 44 h, the reaction was ended by filtering off the enzyme and the filtrate was concentrated by evaporation under reduced pressure to obtain 540 g. Chromatography of the residue on approx. 6 kg of silica gel (1:1 ethyl acetate/n-heptane) gave 184 g of methyl (1R,3S)-2-(3-hydroxycyclohexyloxymethyl)-6-methylbenzoate; >98% ee (HPLC on Chiralpak AD-H 250×4.6; 1 ml/min, heptane/EtOH/$CH_3$CN 25:1:0.5+0.1% TFA); $^1$H NMR ($CDCl_3$), δ = 1.27 (m, 1H), 1.45 (m, 1H), 1.55 (m, 1H), 1.74 (m, 1H), 1.83 (m, 1H), 2.05 (m, 1H), 2.34 (s, 3H), 3.47 (m, 1H), 3.72 (m, 1H), 3.91 (s, 3H), 4.58 (dd, 2H), 7.15 (d, 1H), 7.20 (d, 2H), 7.27 (m, 1H) and 239 g of the (1S,3R)-acetate (93% ee, HPLC on Chiralcel OD/20 250×4.6, 1 ml/min, 100:1:0.5 heptane/EtOH/$CH_3$CN).

Example 3

Synthesis of 4-iodomethyl-2-(3-methoxyphenyl)-5-methyloxazole

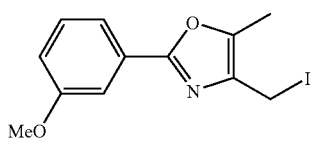

150.0 g (0.63 mol) of 4-chloromethyl-2-(3-methoxyphenyl)-5-methyloxazole were dissolved in 2.7 l of THF and admixed with 106 g (0.71 mol) of NaI.

The mixture was stirred for 4 h and left to stand overnight, the salts were filtered off with suction and the filtrate was concentrated under reduced pressure. After approx. 1–2 hours, the desired iodide solidified, yield: 216 g, mp 58–59° C. $^1$H NMR ($CDCl_3$): δ =2.30 (s, 3H), 3.88 (s, 3H), 4.34 (s, 2H), 6.97 (dd, 1H), 7.34 (t, 1H), 7.52 (d, 1H), 7.58 (d, 1H).

Example 4

Synthesis of Methyl (1R,3S)-2-{3-[2-(3-methoxyphenyl)-5-methyloxazol-4-ylmethoxy]cyclohexyl-1-oxymethyl}-6-methylbenzoate

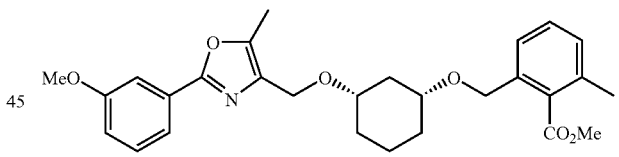

184 g (0.66 mol) of methyl (1R,3S)-2-(3-hydroxycyclohexyloxymethyl)-6-methylbenzoate (see Example 2) were dissolved in 2.2 l of t-BuOMe. 88.0 g (approx. 55%, 1.8 mmol) of NaH were added and the mixture was stirred at 20–22° C. for 45 minutes. 282 g (83.8 mmol) of 4-iodomethyl-2-(3-methoxyphenyl)-5-methyloxazole (see Example 3) were added, and the mixture was stirred at 22° C. for 8 hours and left to stand overnight. The mixture was stirred for a further 4 h and then, with cooling, 200 ml of water were added cautiously, and later a further 1.5 l. The organic phase was removed, dried ($Na_2SO_4$) and concentrated under reduced pressure. 383 g of crude product were obtained and were chromatographed on approx. 6 kg of silica gel (19:1 dichloromethane/acetone), yield: 199 g of a yellowish oil; $^1$H NMR ($CDCl_3$), δ =1.15–1.32 (m, 4H), 1.81 (m, 1H), 2.00 (m, 1H), 2.07 (m, 1H), 2.34 (s, 3H), 2.40 (s, 3H), 2.51 (m, 1H), 3.27 (m, 1H), 3.37 (m, 1H), 3.87 (s, 3H), 3.90 (m, 3H), 4.48 (s, 2H), 4.60 (s, 2H), 6.96 (m, 1H), 7.12–7.35 (m, 4H), 7.53 (s, 1H), 7.58 (d, 1H).

Example 5

Synthesis of (1R,3S)-2-{3-[2-(3-methoxyphenyl)-5-methyloxazol-4-ylmethoxy]cyclohexyl-1-oxymethyl}-6-methylbenzoic acid

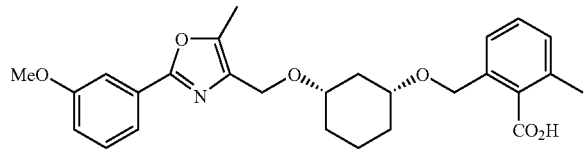

199 g (0.41 mol) of methyl (1R,3S)-2-{3-[2-(3-methoxyphenyl)-5-methyloxazol-4-ylmethoxy]cyclohexyl-1-oxymethyl}-6-methylbenzoate (see Example 4) were dissolved in 2 l of ethanol. 250 ml of 33% NaOH were added and the mixture was heated to reflux for 15 hours. Ethanol was distilled off under reduced pressure, and the residue was dissolved in approx. 2 l of water and washed four times with 500 ml of MTB ether each time. The aqueous phase was acidified to pH 1 using conc. hydrochloric acid with cooling, and the oily product was extracted using 1.5 l of ethyl acetate. The ethyl acetate solution was dried and concentrated under reduced pressure. The residue was dissolved in 1.2 l of DIPE at approx. 40° C. Crystallization and drying under reduced pressure at 60° C. resulted in 132.5 g of the desired carboxylic acid; mp 103–105° C.; >98% ee (HPLC on Chiralpak AD-H 250×4.6; 1 ml/min, 90:7:1 heptane/EtOH/CH$_3$CN+0.1% TFA); $^1$H NMR (CDCl$_3$), δ = 1.14–1.38 (m, 4H), 1.80 (m, 1H), 1.93 (m, 2H), 2.41 (s, 3H), 2.44 (s, 3H), 2.61 (m, 1H), 3.40 (m, 2H), 3.86 (s, 3H), 4.53 (s, 2H), 4.68 (dd, 2H), 6.98 (dd, 1H), 7.17–7.36 (m, 4H), 7.55 (s, 1H), 7.61 (d, 1H).

Example 6

Synthesis of 4-iodomethyl-2-(4-methylphenyl)-5-methyloxazole

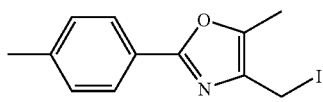

6.0 g of 4-chloromethyl-2-(4-methylphenyl)-5-methyloxazole were dissolved in 120 ml of THF and admixed with 4.18 g (27.9 mmol) of NaI. The mixture was stirred for 3.5 h, a further 1.5 g of NaI were added and the mixture was heated to 35° C. After 30 minutes, the salts were filtered off with suction and the filtrate was concentrated under reduced pressure; yield: 10.1 g, mp 104–105° C.; $^1$H NMR (CDCl$_3$): δ =2.29 (s, 3H), 2.39 (s, 3H), 4.34 (s, 2H), 7.24 (d, 2H), 7.88 (d, 2H).

Example 7

Synthesis of Methyl (1R,3S)-2-{3-[2-(4-methylphenyl)-5-methyloxazol-4-ylmethoxy]cyclohexyl-1-oxymethyl}-6-methylbenzoate

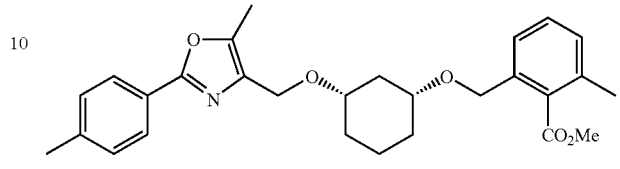

36.0 g (0.129 mol) of methyl (1R,3S)-2-(3-hydroxycyclohexyloxymethyl)-6-methylbenzoate (see Example 2) were dissolved in 430 ml of tBuOMe. 17.2 g (approx. 55%, 0.35 mol) of NaH were added and the mixture was stirred at 23° C. for 30 minutes. 55.1 g (0.166 mol) of 4-iodomethyl-2-(4-methylphenyl)-5-methyloxazole (Example 6) were added. After stirring for 6 hours and leaving to stand over 2 days, 400 ml of water were added and the organic phase was removed. After drying (Na$_2$SO$_4$) and concentrating, the crude product (75 g) was chromatographed on silica gel (approx. 1 kg) (19:1 dichloromethane/acetone), yield: 42 g of the dialkylated 1,3-cyclohexanediol derivative as a yellowish oil; $^1$H NMR (CDCl$_3$), δ =1.16–1.31 (m, 4H), 1.80 (m, 1H), 1.97–2.1 (m, 2H), 2.34 (s, 3H), 2.39 (s, 3H), 2.40 (s, 3H), 2.52 (m, 1H), 3.27 (m, 1H), 3.37 (m, 1H), 3.89 (s, 3H), 4.47 (s, 2H), 4.59 (s, 2H), 7.13 (d, 1H), 7.20–7.28 (m, 4H), 7.88 (d, 1H).

Example 8

Synthesis of (1R,3S)-2-{3-[2-(4-methylphenyl)-5-methyloxazol-4-yl-methoxy]cyclohexyl-1-oxymethyl}-6-methylbenzoic acid

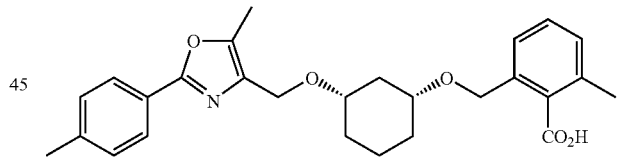

42.0 g (0.09 mol) of methyl (1R,3S)-2-{3-[2-(4-methylphenyl)-5-methyloxazol-4-ylmethoxy]cyclohexyl-1-oxymethyl}-6-methylbenzoate (see Example 7) were dissolved in 420 ml of ethanol. 45 ml of 33% NaOH were added and the mixture was heated to reflux for approx. 20 hours. Ethanol was distilled off under reduced pressure, the residue was dissolved in 500 ml of water and the solution was washed four times with in each case 100 ml of MTB ether. The aqueous phase was acidified (pH 1) using conc. hydrochloric acid with cooling and the oily product was extracted using ethyl acetate. The ethyl acetate solution was dried and concentrated under reduced pressure. The residue was dissolved in 250 ml of DIPE with heating. On cooling, the crystallization set in. When the crystallization had ended, and after drying under reduced pressure at 60° C., 28.4 g of the desired carboxylic acid were obtained; mp 117–119° C.; >98% ee (HPLC on Chiralpak AD-H 250×4.6; 1 ml/min, 90:7:1 heptane/EtOH/CH$_3$CN+0.1% TFA); $^1$H NMR (CDCl$_3$), δ =1.14–1.36 (m, 4H), 1.80 (m, 1H), 1.91 (m, 2H), 2.39 (s, 3H), 2.40 (s, 3H), 2.46 (s, 3H), 2.64 (m, 1H), 3.40 (m, 2H), 4.54 (s, 2H), 4.68 (dd, 2H), 7.17–7.30 (m, 5H), 7.91 (d, 2H).

Example 9

Synthesis of 4-iodomethyl-2-(3-methylphenyl)-5-methyloxazole

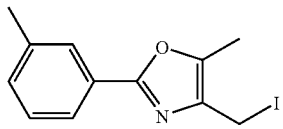

6.0 g of 4-chloromethyl-2-(4-methylphenyl)-5-methyloxazole were dissolved in 120 ml THF and admixed with 4.5 g (30 mmol) of NaI. The mixture was stirred for 5 h and then left to stand overnight. The removal of the solid and concentration of the filtrate under reduced pressure gave 10.2 g of the desired iodide; mp~32° C.; $^1$H NMR (CDCl$_3$): δ =2.30 (s, 3H), 2.40 (s, 3H), 4.34 (s, 2H), 7.24 (d, 1H), 7.32 (t, 1H), 7.77 (d, 1H), 7.83 (d, 1H).

Example 10

Synthesis of Methyl (1R,3S)-2-{3-[2-(3-methylphenyl)-5-methyloxazol-4-ylmethoxy]cyclohexyl-1-oxymethyl}-6-methylbenzoate

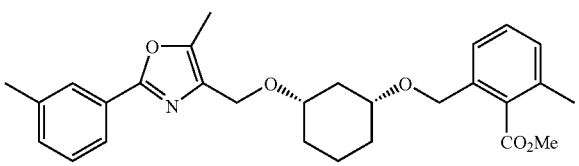

36.0 g (0.129 mol) of methyl (1R,3S)-2-(3-hydroxycyclohexyloxymethyl)-6-methylbenzoate (see Example 2) were dissolved in 430 ml of tBuOMe. 17.19 g (approx. 55%, 0.35 mol) of NaH were added and the mixture was stirred at 20–22° C. for 30 minutes. 55.1 g (0.166 mol) of 4-iodomethyl-2-(3-methylphenyl)-5-methyloxazole (see Example 9) were added. After stirring for 6 hours and leaving to stand over 2 days, 400 ml of water were added with cooling and the organic phase was removed. After drying (Na$_2$SO$_4$) and concentrating, the crude product (75 g) was chromatographed on silica gel (1.2 kg) (19:1 dichloromethane/acetone), yield: 49 g of methyl (1R,3S)-2-{3-[2-(3-methylphenyl)-5-methyloxazol-4-ylmethoxy]cyclohexyl-1-oxymethyl}-6-methylbenzoate; $^1$H NMR (CDCl$_3$), δ = 1.13–1.31 (m, 4H), 1.80 (m, 1H), 1.97–2.1 (m, 2H), 2.34 (s, 3H), 2.40 (s, 3H), 2.41 (s, 3H), 2.52 (m, 1H), 3.27 (m, 1H), 3.37 (m, 1H), 3.90 (s, 3H), 4.48 (s, 2H), 4.59 (s, 2H), 7.12–7.33 (m, 4H), 7.78 (d, 1H), 7.84 (s, 1H).

Example 11

Synthesis of (1R,3S)-2-{3-[2-(3-methylphenyl)-5-methyloxazol-4-ylmethoxy]cyclohexyl-1-oxymethyl}-6-methylbenzoic acid

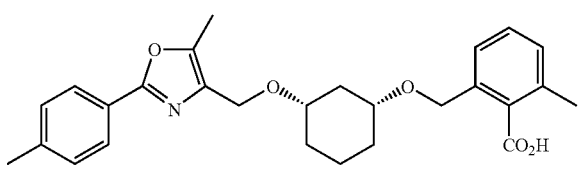

49.0 g (0.09 mol) of methyl (1R,3S)-2-{3-[2-(3-methylphenyl)-5-methyloxazol-4-ylmethoxy]cyclohexyl-1-oxymethyl}-6-methylbenzoate (see Example 10) were dissolved in 500 ml of ethanol. 50 ml of 33% NaOH were added and the mixture was heated to reflux for approx. 14 hours. Ethanol was dissolved off under reduced pressure, the residue was dissolved in 500 ml of water and the solution was washed three times with in each case 150 ml of MTB ether. The aqueous phase was acidified (pH 1) using conc. hydrochloric acid with cooling, and the oily product was extracted with ethyl acetate. The ethyl acetate solution was dried and concentrated under reduced pressure. The residue was dissolved in 250 ml of DIPE with heating. On cooling, crystallization set in. When the crystallization has ended, and after drying under reduced pressure at 60° C., 29.9 g of the desired carboxylic acid are obtained; mp 109–111° C.; >98% ee (HPLC on Chiralpak AD-H 250×4.6; 1 ml/min, 90:7:1 heptane/EtOH/CH$_3$CN+0.1% TFA); $^1$H NMR (CDCl$_3$), δ =1.14–1.36 (m, 4H), 1.80 (m, 1H), 1.93 (m, 2H), 2.40 (s, 2×3H), 2.45 (s, 3H), 2.64 (m, 1H), 3.40 (m, 2H), 4.53 (s, 2H), 4.68 (dd, 2H), 7.17–7.34 (m, 5H), 7.81 (d, 1H), 7.85 (s, 1H).

Scheme IIa

Example 12

Optical Resolution of cis-3-[2-(3-methoxyphenyl)-5-methyloxazol4-ylmethoxy]cyclohexan-1-ol

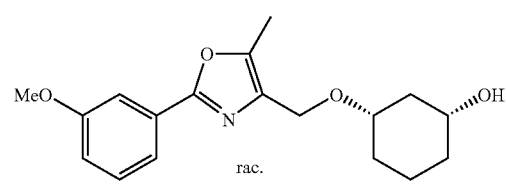

24.9 g of the racemic cis-3-[2-(3-methoxyphenyl)-5-methyloxazol-4-ylmethoxy]cyclohexan-1-ol (prepared by alkylating cis-1,3-cyclohexanediol with 4-iodomethyl-2-(3-methoxyphenyl)-5-methyloxazole) were dissolved in 100 ml of vinyl acetate, admixed with 1.0 g of Chirazyme L-2, lyo., and stirred at 20–23° C. After about 30 minutes, the enzyme was filtered off and the solution concentrated under reduced pressure, crude product: 25.8 g. After chromatography on silica gel (10:1–0:1 n-heptane/ethyl acetate), 13.7 g of (1S,3R)-3-[2-(3-methoxyphenyl)-5-methyloxazol-4-ylmethoxy]cyclohexan-1-ol and 11.3 g of the (1R,3S)-acetyl compound were obtained.

Example 13

Preparation of (1R,3S)-3-[2-(3-methoxyphenyl)-5-methyloxazol-4-yl-methoxy]cyclohexan-1-ol

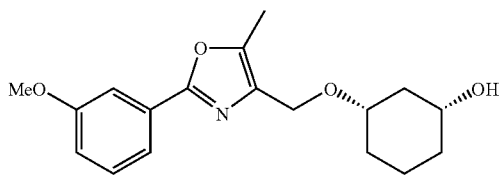

11.2 g of the (1R,3S)-acetate from Example 12 were dissolved in approx. 100 ml of MeOH, admixed with 0.5 ml of NaOMe (30%) and stirred at 20–23° C. After 3.5 h, the mixture was neutralized with concentrated acetic acid, taken up with ethyl acetate, washed with NaHCO$_3$, dried over Na$_2$SO$_4$ and concentrated under reduced pressure. After filtration through silica gel (10:1–0:1 n-heptane/ethyl acetate), 8.8 g of (1R,3S)-3-[2-(3-methoxyphenyl)-5-methyloxazol-4-ylmethoxy]cyclohexan-1-ol having 92% ee (HPLC on Chiralpak AD-H 250×4.6; 1 ml/min, 90:7:1 heptane/EtOH/CH$_3$CN+0.1% TFA) were obtained.

Example 14

Synthesis of Methyl (1R,3S)-2-{3-[2-(3-methoxyphenyl)-5-methyloxazol-4-ylmethoxy]cyclohexyl-1-oxymethyl}-6-methylbenzoate

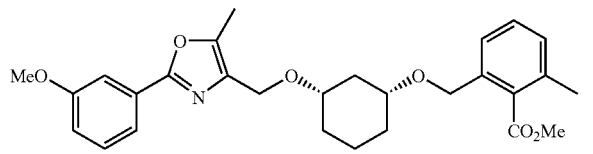

1.4 g (4.4 mmol) of (1R,3S)-3-[2-(3-methoxyphenyl)-5-methyloxazol-4-ylmethoxy]cyclohexanol (see Example 13) were taken up in 15 ml of tBuOMe, admixed at 24–27° C. with 1.20 g (10.7 mmol) of KOtBu and stirred for approx. 30 minutes. The mixture was cooled to 0–5° C., 1.89 g (approx. 94%, approx. 7.4 mmol) of methyl 2-bromomethyl-6-methylbenzoate were added dropwise and the mixture was stirred at 0–5° C. for an initial 30 minutes. Without further cooling, the reaction mixture had a temperature of approx. 20° C. after 1.5 hours. After stirring overnight and adding approx. 200 mg of KOtBu, the reaction was complete after stirring at 22° C. for a further hour. Distilling off the solvent under reduced pressure, partitioning the residue between water and tBuOMe and drying the product-containing organic phase resulted, after concentrating under reduced pressure, in 1.6 g of methyl (1R,3S)-2-{3-[2-(3-methoxyphenyl)-5-methyloxazol-4-ylmethoxy]cyclohexyl-1-oxymethyl}-6-methylbenzoate as a yellowish oil; $^1$H NMR (CDCl$_3$), δ =1.15–1.32 (m, 4H), 1.81 (m, 1H), 2.00 (m, 1H), 2.07 (m, 1H), 2.34 (s, 3H), 2.40 (s, 3H), 2.51 (m, 1H), 3.27 (m, 1H), 3.37 (m, 1H), 3.87 (s, 3H), 3.90 (s, 3H), 4.48 (s, 2H), 4.60 (s, 2H), 6.96 (m, 1H), 7.12–7.35 (m, 4H), 7.53–7.60 (m, 2H).

Example 15

Synthesis of Methyl (1S,3R)-2-{3-[2-(3-methoxyphenyl)-5-methyloxazol-4-ylmethoxy]cyclohexyl-1-oxymethyl}-6-methylbenzoate

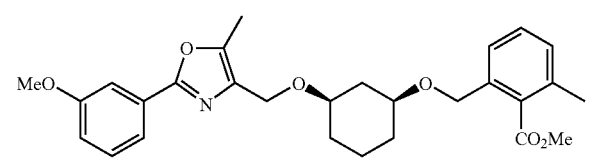

Starting from (1S,3R)-3-[2-(3-methoxyphenyl)-5-methyloxazol-4-yl-methoxy]cyclohexan-1-ol from Example 12, alkylation in a similar manner to Example 14 gives (1S,3R)-2-{3-[2-(3-methoxyphenyl)-5-methyloxazol-4-ylmethoxy]cyclohexyl-1-oxymethyl}-6-methylbenzoate; the $^1$H NMR data agree with those in Example 14.

Example 16

Optical resolution of cis-3-[2-(4-fluorophenyl)oxazol4-ylmethoxy]-cyclohexan-1-ol, preparation of (1S,3R)-3-[2-(4-fluorophenyl)oxazol-4-ylmethoxy]cyclohexan-1-ol

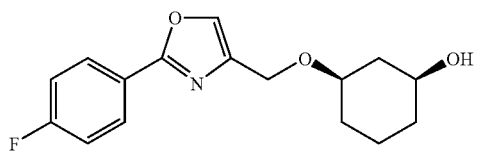

30 mg of racemic cis-3-[2-(4-fluorophenyl)oxazol-4-ylmethoxy]cyclohexan-1-ol were taken up in about 3 ml dichloromethane, admixed with 60 mg of p-nitrophenyl acetate and stirred at 20–23° C. with 10 mg of Novozyme 435. After 70 h, the immobilized enzyme was filtered off. The determination of the optical purity directly from the reaction mixture which had been concentrated by evaporation gave >95% ee (HPLC on Chiralpak AD 250×4.6; 1 ml/min, acetonitrile) for (1S,3R)-3-[2-(4-fluorophenyl)oxazol-4-ylmethoxy]cyclohexan-1-ol and 95% ee for the (1R,3S)-acetate (HPLC on Chiralpak AD 250×4.6; 1 ml/min, acetonitrile). To isolate (1S,3R)-3-[2-(4-fluorophenyl)oxazol-4-ylmethoxy]cyclohexan-1-ol, the crude mixture was chromatographed on silica gel (ethyl acetate/n-heptane); yield 12 mg, 96% ee.

Example 17

Synthesis of methyl (1S,3R)-2-{3-[2-(4-fluorophenyl)oxazol-4-ylmethoxy-cyclohexyl-1-oxymethyl}6-methylbenzoate

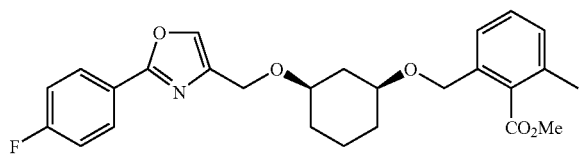

Starting from (1S,3R)-3-[2-(4-fluorophenyl)oxazol-4-ylmethoxy]cyclohexan-1-ol from Example 16, alkylation with methyl 2-bromomethyl-6-methylbenzoate gives methyl (1S,3R)-2-{3-[2-(4-fluorophenyl)oxazol-4-yl-methoxy]cyclohexyl-1-oxymethyl}-6-methylbenzoate (see Example 35).

Example 18

Optical Resolution of 3-[2-(4-methylphenyl)-5-methyloxazol-4-yl-methoxy]cyclohexan-1-ol

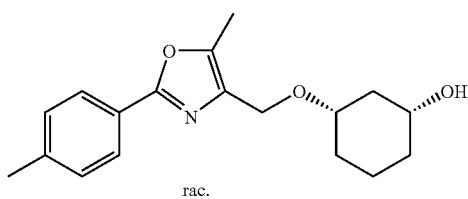

rac.

where $R^4$=p-Me-, $R^5$=H and $R^3$=Me)

16.3 g of the racemic 3-[2-(4-methylphenyl)-5-methyloxazol-4-yl-methoxy]cyclohexan-1-ol were dissolved in 100 ml of vinyl acetate, admixed with 1.9 g of Chirazyme L-2, lyo., and stirred at 20–23° C. After about 30 minutes, the enzyme was filtered off and the solution concentrated under reduced pressure, crude product: 16.6 g. After chromatography on silica gel (10:1–0:1 n-heptane/ethyl acetate), 8.6 g of (1S,3R)-3-[2-(4-methylphenyl)-5-methyloxazol-4-yl-methoxy]cyclohexan-1-ol and 6.8 g of the (1R,3S)-acetate are obtained.

Example 19

Preparation of (1R,3S)-3-[2-(4-methylphenyl)-5-methyloxazol-4-ylmethoxy]-cyclohexan-1-ol

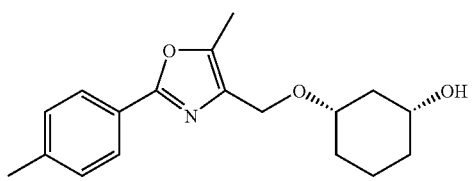

6.8 g of the (1R,3S)-acetyl compound from the Example 18 were dissolved in approx. 65 ml of MeOH, admixed with 0.32 ml of NaOMe (30%) and stirred at 20–23° C. After 4 h, the mixture was neutralized with acetic acid, concentrated under reduced pressure, taken up with ethyl acetate, washed with NaHCO$_3$, dried (Na$_2$SO$_4$) and concentrated under reduced pressure. After filtration through silica gel (10:1–0:1 n-heptane/ethyl acetate), 8.8 g of the desired (1R,3S)-3-[2-(4-methylphenyl)-5-methyloxazol4-ylmethoxy]-cyclohexan-1-ol with 95% ee (HPLC on Chiralpak AD 250×4.6; 1 ml/min, 90:7:1 heptane/EtOH/CH$_3$CN+0.1% TFA) are obtained.

Example 20

Optical resolution of cis-3-[2-phenyl-5-methyloxazol-4-ylmethoxy]-cyclohexan-1-ol

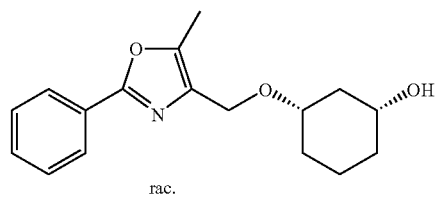

rac.

2.0 g of racemic cis-3-[2-phenyl-5-methyloxazol-4-yl-methoxy]cyclohexan-1-ol were dissolved in 50 ml of vinyl acetate, admixed with 0.1 g of Chirazyme L-2, lyo., and stirred at 20–23° C. After about 5 h, the enzyme was filtered off and the solution concentrated under reduced pressure. After chromatography on silica gel (2:1–1:2 n-heptane/ethyl acetate), 1.0 g of (1S,3R)-3-[2-phenyl-5-methyloxazol-4-ylmethoxy]-cyclohexan-1-ol was obtained as a bright yellow solid and 0.96 g of the acetylated (1R,3S) compound as a colorless oil.

Example 21

Preparation of (1R,3S)-3-[2-phenyl-5-methyloxazol-4-ylmethoxy]-cyclohexan-1-ol

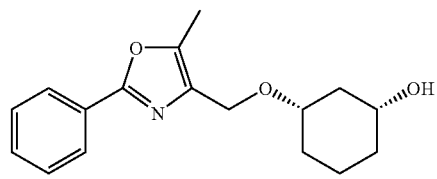

0.96 g of the (1R,3S)-acetyl compound from Example 20 was dissolved in approx. 5–10 ml of MeOH, admixed with 0.1 ml of NaOMe (30%) and stirred at 20–23° C. After 3 h, the mixture was neutralized with acetic acid and concentrated under reduced pressure, taken up with ethyl acetate, washed with saturated NaHCO$_3$, dried (MgSO$_4$) and concentrated under reduced pressure. After filtration through silica gel (10:1–0:1 n-heptane/ethyl acetate), 0.84 g of the desired (1R,3S)-3-[2-phenyl-5-methyloxazol-4-ylmethoxy]cyclohexan-1-ol having 95% ee (HPLC on Chiralpak AD 250×4.6; 1 ml/min, 25:1:0.5 heptane/EtOH/CH$_3$CN+0.1% TFA) was obtained.

Example 22

Optical resolution of cis-3-[2-(4-methoxyphenyl)-5-methyloxazol-4-yl-methoxy]cyclohexan-1-ol

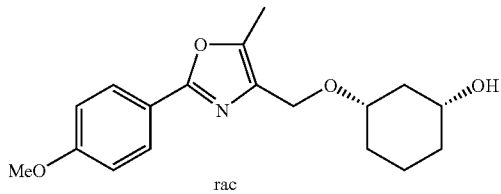

2.0 g of the racemic cis-3-[2-(4-methoxyphenyl)-5-methyloxazol-4-yl-methoxy]cyclohexan-1-ol were dissolved in 50 ml of vinyl acetate, admixed with 0.1 g of Chirazyme L-2, lyo., and stirred at 20–23° C. After about 5 h, the enzyme was filtered off and the solution concentrated under reduced pressure. After chromatography on silica gel (2:1–1:2 n-heptane/ethyl acetate), 1.16 g of (1S,3R)-3-[2-(4-methoxyphenyl)-5-methyloxazol-4-ylmethoxy]cyclohexan-1-ol and 0.79 g of the (1R,3S)-acetate were obtained.

Example 23

Preparation of (1R,3S)-3-[2-(4-methoxyphenyl)-5-methyloxazol-4-yl-methoxy]cyclohexan-1-ol

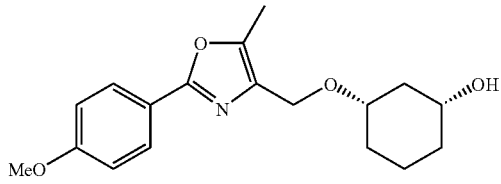

0.79 g of acetate from Example 22 were dissolved in approx. 5–10 ml of MeOH, admixed with 0.1 ml of NaOMe (30%) and stirred at 20–23° C. After 3 h, the mixture was neutralized with dilute acetic acid and concentrated under reduced pressure, taken up with ethyl acetate, washed with saturated NaHCO₃, dried (MgSO₄) and concentrated under reduced pressure. After filtration through silica gel (10:1–0:1 n-heptane/ethyl acetate), 0.84 g of (1R,3S)-3-[2-(4-methoxyphenyl)-5-methyloxazol-4-ylmethoxy]cyclohexan-1-ol were obtained as a yellow oil having 92% ee (HPLC on Chiralpak AD 250×4.6; 1 ml/min, 90:7:1 heptane/EtOH/CH₃CN+0.1% TFA).

Example 24

Optical resolution of cis-3-[2-(4-fluorophenyl)-5-methyloxazol-4-yl-methoxy]cyclohexan-1-ol

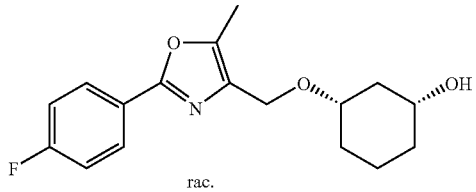

1.70 g of the racemic cis-3-[2-(4-fluorophenyl)-5-methyloxazol-4-yl-methoxy]cyclohexan-1-ol were dissolved in 50 ml of vinyl acetate, admixed with 0.1 g of Chirazyme L-2, lyo., and stirred at 20–23° C. After about 1.5 h, the enzyme was filtered off and the solution concentrated under reduced pressure. After chromatography on silica gel (5:1–1:1 n-heptane/ethyl acetate), 1.0 g of (1S,3R)-3-[2-(4-fluorophenyl)-5-methyloxazol-4-yl-methoxy]cyclohexan-1-ol and 0.75 g of the (1R,3S)-acetate were obtained.

Example 25

Preparation of (1R,3S)-3-[2-(4-fluorophenyl)-5-methyloxazol-4-ylmethoxy]-cyclohexan-1-ol

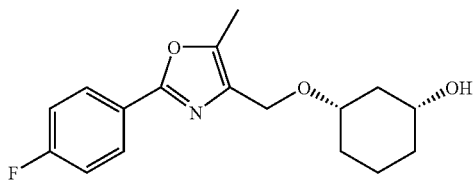

0.75 g of acetate from Example 24 was dissolved in approx. 30 ml of MeOH, admixed with 0.2 ml of NaOMe (30%) and stirred at 20–23° C. After 1 h, the mixture was neutralized with dilute acetic acid and concentrated under reduced pressure, taken up with ethyl acetate, washed with saturated NaHCO₃, dried (MgSO₄) and concentrated under reduced pressure, yield: 0.59 g of (1R,3S)-3-[2-(4-fluorophenyl)-5-methyloxazol4-ylmethoxy]cyclohexan-1-ol as a white solid having 94% ee (HPLC on Chiralpak OD/19 250×4.6; 1 ml/min, 110:2:1 heptane/EtOH/CH₃CN+0.05% TFA).

Scheme IIb

Example 26

Stereoselective hydrolysis of 3-[2-(4-fluorophenyl)oxazol-4-ylmethoxyl]-cyclohexyl acetate, preparation of (1R,3S)-3-[2-(4-fluorophenyl)oxazol-4-yl-methoxy]cyclohexan-1-ol

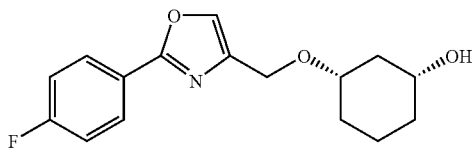

Approx. 10 mg of 3-[2-(4-fluorophenyl)oxazol-4-yl-methoxyl]cyclohexyl acetate (prepared by reacting 3-benzyloxycyclohexan-1-ol with acetic anhydride, in a similar manner to the synthesis of mono(3-benzyloxycyclohexyl) glutarate see Example 39) were taken up in 2 ml of phosphate buffer (0.1 M, pH=7.0) and 2 ml of DME and stirred with approx. 5 mg of Chirazyme L-2, lyo., at 20–23° C. for approx. 20–24 h. The reaction mixture was extracted with dichloromethane. The organic phase was admixed with toluene and concentrated by evaporation under reduced pressure. The determination of the optical purity for (1R, 3S)-3-[2-(4-fluorophenyl)oxazol4-ylmethoxy]cyclohexan-1-ol gave 99.4% ee (HPLC on Chiralpak AD 250×4.6; 1 ml/min, acetonitrile) and 98.9% ee for the (1S,3R)-acetate (HPLC on Chiralcel OD 250×4.6; 1 ml/min, 110:5:1 heptane/EtOH/CH₃CN+0.1% TFA).

Scheme IIIa

Example 27

Synthesis of racemic cis-3-benzyloxycyclohexan-1-ol

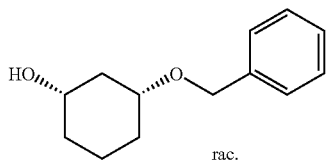

rac.

150.0 g (1.29 mol) of cis-1,3-cyclohexanediol were dissolved in 1.5 l of NMP, admixed with 111.6 g (0.99 mol) of potassium tert-butoxide (KOtBu) and stirred at 25–27° C. After about 30 minutes, the mixture was cooled to 0° C. and admixed dropwise with 78.1 g (0.46 mol) of benzyl bromide. The mixture was stirred at approx. 0° C. for 15 min and then 1.5 l of water were added. After washing three times with 700 ml of n-heptane and discarding the n-heptane solutions, the aqueous solution was extracted four times with 500 ml of MTBE. The combined MTBE phases were washed twice with in each case 1 l of water, dried ($Na_2SO_4$) and subsequently concentrated by evaporation under reduced pressure. 48.0 g of the desired compound were obtained as a clear, yellow oil; $^1$H NMR ($CDCl_3$), δ =1.29 (m, 1H), 1.43–1.93 (m, 6H), 2.06 (m, 1H), 2.55 (s (br.), 1H), 3.56 (m, 1H), 3.74 (br, 1H), 4.55 (dd, 2H), 7.25–7.36 (m, 5H).

Example 28

Optical resolution of 3-benzyloxycyclohexan-1-ol

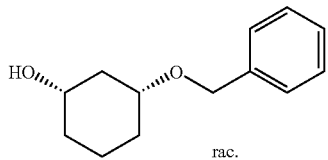

rac.

20.3 g of cis-3-benzyloxycyclohexan-1-ol were dissolved in 35 ml of vinyl acetate and 125 ml of methylene chloride, admixed with 2.0 g of Novozym 435 and stirred at 20–23° C. for 6 h. After leaving to stand overnight, the enzyme was filtered off. A sample was withdrawn and concentrated by evaporation under reduced pressure. The enantiomeric excess of (1S,3R)-3-benzyloxycyclohexan-1-ol was >99% (HPLC on Chiralpak AD-H 250×4.6; 1 ml/min, 25:1:0.5 heptane/EtOH/$CH_3CN$+0.1% TFA), and the enantiomeric excess of the (1R,3S)-acetate was 78% (HPLC on Chiralcel OD 250×4.6; 1 ml/min, 100:1:0.5 heptane/EtOH/$CH_3CN$).

Example 29

Optical resolution of 3-benzyloxycyclohexan-1-ol

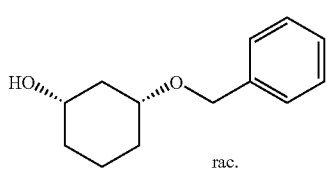

rac.

100.0 g of cis-3-benzyloxycyclohexan-1-ol were dissolved in 170 ml of vinyl acetate and 630 ml of methylene chloride, admixed with 5.0 g of Novozym 435 and stirred at 20–23° C. for 26 h. The enzyme was filtered off, and a sample was withdrawn and concentrated by evaporation under reduced pressure. The enantiomeric excess of (1S,3R)-3-benzyloxycyclohexan-1-ol was >99% (HPLC on Chiralpak AD-H 250×4.6; 1 ml/min, 25:1:0.5 heptane/EtOH/$CH_3CN$+0.1% TFA), and the enantiomeric excess of the (1R,3S)-acetate was 90% (HPLC on Chiralcel OD 250×4.6; 1 ml/min, 100:1:0.5 heptane/EtOH/$CH_3CN$).

Example 30

Isolation of (1S,3R)-3-benzyloxycyclohexan-1-ol, separation of the mixture of acetate and alcohol with pyridine-$SO_3$ 1.9 g of the crude acetate/alcohol mixture from the stereoselective enzymatic acetylation of 3-benzyloxycyclohexan-1-ol (from Example 29) were stirred with 2 g of pyridine-$SO_3$ at 20–22° C. in 10 ml of pyridine and 2 ml of DMF. After 4 h, the conversion of the benzylcyclohexanol to the pyridine salt of the sulfuric ester was virtually quantitative. The reaction mixture was diluted with 40 ml of water and extracted twice with approx. 20 ml of MTBE. The MTBE phases contain the unchanged (1R,3S)-acetate quantitatively. The remaining, acetate-free aqueous phase was concentrated by evaporation under reduced pressure. The residue was admixed with MTBE, and the sulfation product solidified; yield: 2.7 g.

2.7 g of pyridine salt of the sulfuric ester of (1S,3R)-benzylcyclohexan-1-ol were stirred at 55° C. in 45 ml of THF, 4 ml of water and 1 ml of conc. sulfuric acid for 2 h. The mixture was admixed with 40 ml of water, approx. 10 ml of MTBE were added, the phases were separated and the aqueous phase was extracted once with MTBE. The combined organic phases were dried ($Na_2SO_4$) and concentrated by evaporation; yield: 640 mg of a bright yellow oil. The NMR data agree with the data quoted in Example 16; the testing of the optical purity gave >99% ee.

Example 31

Isolation of (1S,3R)-3-benzyloxycyclohexan-1-ol, separation of the mixture of acetate and alcohol by extraction 10 g of the crude acetate/alcohol mixture from Example 29 were taken up in approx. 90 ml of methanol and approx. 70 ml of water and washed three times with in each case approx. 50 ml of n-heptane. The combined heptane phases (contain predominantly the acetate) are extracted with 50 ml of 1:1 methanol/water. The combined aqueous phases are washed again with n-heptane. After concentrating the aqueous phase, 3.6 g of the desired (1S,3R)-3-benzyloxycyclohexan-1-ol were obtained, and the concentration of the combined heptane phases gave 5.5 g of the (1R,3S)-acetate.

Example 32

Synthesis of 4-iodomethyl-2-(4-fluorophenyl)oxazole

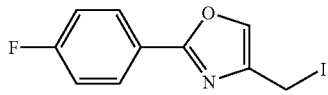

4.0 g (18.9 mmol) of 4-chloromethyl-2-(4-fluorophenyl)oxazole were dissolved in 80 ml of THF and admixed with 3.18 g (21.2 mmol) of NaI. The mixture was stirred at 20–23° C. for 3 h and at 50° C. for about 12 h, the salts were filtered off with suction and the filtrate was concentrated under reduced pressure, yield: 6.1 g. The product crystallized; mp 100–102° C.; $^1$H NMR (CDCl$_3$): δ =4.34 (s, 2H), 6.97 (dd, 1H), 7.14 (m, 2H), 7.68 (s, 1H), 8.03 (m, 2H).

Example 33

Synthesis of (1S,3R)-4-(3-benzyloxycyclohexyl-1-oxymethyl)-2-(4-fluorophenyl)oxazole

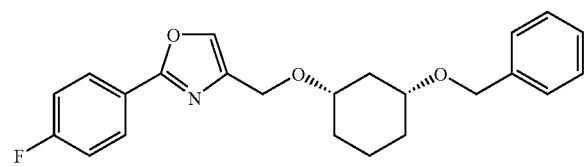

2.0 g (9.7 mmol) of (1S,3R)-3-benzyloxycyclohexan-1-ol were dissolved in 35 ml of tBuOMe. 1.3 g (approx. 55%, 43.7 mmol) of NaH were added and the mixture was stirred at 22° C. for 60 minutes. 3.9 g (12.9 mmol) of 4-iodomethyl-2-(4-fluorophenyl)oxazole (Example 32) were added and the mixture was stirred at 22–23° C. for about 3 hours. After leaving to stand overnight, the mixture was stirred at 22–23° C. for a further 11 h. Water (approx. 30 ml) was added with cooling and the organic phase was removed. Drying (Na$_2$SO$_4$), concentrating (crude yield: 4.5 g) and chromatography on silica gel (19:1 dichloromethane/acetone) gave 2.4 g of the desired, cis-configured, optically pure, dialkylated 1,3-cyclohexanediol derivative as a white solid; mp 61–62° C.; $^1$H NMR (CDCl$_3$), δ =1.11–1.39 (m, 4H), 1.82 (m, 1H), 2.07 (m, 2H), 2.55 (m, 1H), 3.38 (m, 2H), 4.55 (s, 2H), 4.57 (s, 2H), 7.13 (m, 2H), 7.25–7.35 (m, 5H), 7.63 (s, 1H), 8.02 (m, 2H).

Example 34

Synthesis of (1R,3S)-3-[2-(4-fluorophenyl)oxazol-4-ylmethoxy]cyclohexanol by hydrogenation

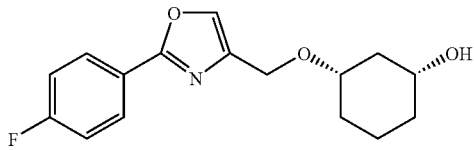

2.4 g of (1S,3R)-4-(3-benzyloxycyclohexyl-1-oxymethyl)-2-(4-fluorophenyl)-oxazole were dissolved in approx. 40 ml of methanol, admixed with a spatula tip of Pd/C (10%, comprising 50% water) [lacuna] hydrogenated at 20–23° C. under atmospheric pressure for approx. 8 hours. Filtering off the catalyst and concentrating the remaining solution gave 1.8 g of the desired cis-configured, monoalkylated 1,3-cyclohexanediol derivative as an oil which crystallized when DIPE was added; yield 1.6 g; mp 81–82° C.; $^1$H NMR (CDCl$_3$), δ =1.25–2.14 (m, 9H), 3.63 (m, 1H), 3.75 (m, 1H), 4.55 (dd, 2H), 7.13 (m, 2H), 7.64 (s, 1H), 8.02 (m, 2H); MS (DCI): 292.3 (100%).

Example 35

Synthesis of methyl (1R,3S)-2-{3-[2-(4-fluorophenyl)oxazol-4-ylmethoxy]-cyclohexyl-1-oxymethyl}-6-methylbenzoate

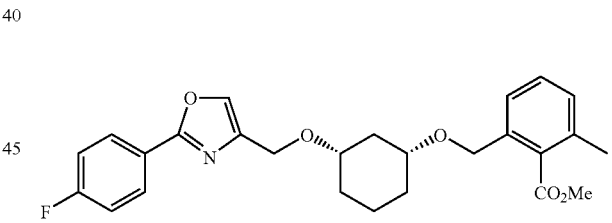

0.8 g (2.75 mmol) of (1R,3S)-3-[2-(4-fluorophenyl)oxazol-4-ylmethoxy]-cyclohexanol (from Example 34) was taken up in 10 ml of tBuOMe, admixed with 0.78 g (6.95 mmol) of KOtBu and stirred at 22–27° C. for approx. 30 minutes. The mixture was cooled to 0–5° C., 1.24 g (approx. 94%, approx. 4.8 mmol) of methyl 2-bromomethyl-6-methylbenzoate were added dropwise, the mixture was stirred initially at 3° C. for 2 hours and at 20° C. for a further hour. The mixture is left to stir overnight at 18–21° C., then the solvent is distilled off. The residue is partitioned between water and tBuOMe. The organic phase is dried (Na$_2$SO$_4$) and concentrated under reduced pressure; yield: 1.04 g of methyl (1R,3S)-2-{3-[2-(4-fluorophenyl)oxazol-4-ylmethoxy]cyclohexyl-1-oxymethyl}-6-methyl-benzoate as a yellowish oil; $^1$H NMR (CDCl$_3$), δ =1.15–1.32 (m, 4H), 1.82 (m, 1H), 1.98–2.1 (m, 2H), 2.34 (s, 3H), 2.50 (m, 1H), 3.27 (m, 1H), 3.39 (m, 1H), 3.90 (s, 3H), 4.54 (s, 2H), 4.60 (s, 2H), 7.11–7.30 (m, 5H), 7.63 (s, 1H), 8.02 (m, 2H).

Example 36

Synthesis of (1S,3R)4-(3-benzyloxy-cyclohexyl-1-oxymethyl)-2-(3-methoxyphenyl)-5-methyloxazole

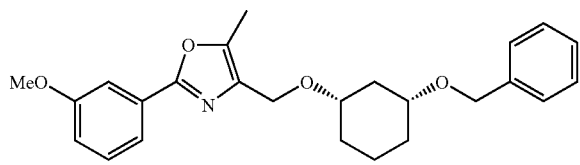

4.6 g (22.3 mmol) of (1S,3R)-3-benzyloxycyclohexan-1-ol were dissolved in 70 ml of chlorobenzene. 6.6 g (58.8 mmol) of KOtBu were added, the mixture was stirred at 22° C. for 30 minutes and then 10.3 g (31.3 mmol) of 4-iodomethyl-2-(3-methoxyphenyl)-5-methyloxazole were added. The temperature rose to 35° C. The reaction was cooled slightly and stirred at 22–23° C. for a further 2 hours. After the chlorobenzene had been distilled off under reduced pressure, the residue was partitioned between tBuOMe and water. The organic phase was dried ($Na_2SO_4$) and concentrated under reduced pressure; crude yield: 10.6 g. The substance was used in the next reaction (hydrogenation, see Example 37) without further purification.

Example 37

Synthesis of (1R,3S)-3-[2-(3-methoxyphenyl)oxazol-4-ylmethoxy]-cyclohexanol by hydrogenation

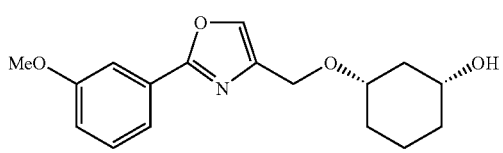

10.5 g of (1S,3R)-4-(3-benzyloxycyclohexyl-1-oxymethyl)-2-(3-methoxy-phenyl)oxazole were dissolved in approx. 120 ml of methanol, admixed with 2 g of Pd/C (10%, having 50% of water) and hydrogenated at 20–23° C. under atmospheric pressure overnight. Filtering off the catalyst and concentrating the remaining solution, partitioning between MTB ether and water and drying the organic phase gave 6.4 g of the desired cis-configured, monoalkylated 1,3-cyclohexanediol derivative as a yellow oil. 1 g of the substance was chromatographed on silica gel (ethyl acetate): 0.8 g of a colorless oil were obtained; $^1$H-NMR ($CDCl_3$), δ=1.25–1.90 (m, 7H), 2.12 (m, 1H), 2.41 (s, 3H), 3.61 (m, 1H), 3.75 (m, 1H), 3.87 (s, 3H), 4.48 (dd, 2H), 6.96 (d, 1H), 7.33 (t, 1H), 7.53 (s, 1H), 7.58 (d, 1H); MS (ES+): 318.27 (83%), 243.18 (100%).

Example 38

Synthesis of methyl (1R,3S)-2-{3-[2-(3-methoxyphenyl)-5-methyloxazol-4-ylmethoxy]cyclohexyl-1-oxymethyl}-6-methylbenzoate

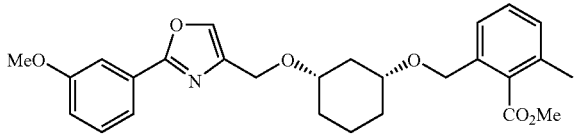

136 mg (0.4 mmol) of (1R,3S)-3-[2-(3-methoxyphenyl)-5-methyloxazol-4-yl-methoxy]cyclohexanol (from Example 37, hydrogenation) were dissolved in 1 ml of chlorobenzene, admixed at 24–27° C. with 120 mg (1.07 mmol) of KOtBu and stirred for approx. 30 minutes. The mixture was cooled to 0–5° C., 189 mg (approx. 94%, approx. 0.78 mmol) of methyl 2-bromomethyl-6-methylbenzoate were added dropwise and the mixture was stirred at 0–5° C. for an initial 30 minutes. Without further cooling, the reaction mixture had a temperature of approx. 20° C. after 1.5 hours. After leaving to stand overnight and adding approx. 20 mg of KOtBu, the reaction was complete after a further hour of stirring at 22° C. Distilling off the chlorobenzene under reduced pressure, partitioning the residue between water and tBuOMe and drying the product-containing organic phase gave, after concentrating under reduced pressure, 160 mg of methyl (1R,3S)-2-{3-[2-(3-methoxyphenyl)-5-methyloxazol-4-ylmethoxy]cyclohexyl-1-oxymethyl}-6-methylbenzoate as a yellowish oil; $^1$H-NMR ($CDCl_3$), δ=1.15–1.32 (m, 4H), 1.81 (m, 1H), 2.00 (m, 1H), 2.06 (m, 1H), 2.34 (s, 3H), 2.40 (s, 3H), 2.51 (m, 1H), 3.27 (m, 1H), 3.36 (m, 1H), 3.87 (s, 3H), 3.90 (m, 3H), 4.48 (s, 2H), 4.60 (s, 2H), 6.96 (m, 1H), 7.12–7.35 (m, 4H), 7.53–7.60 (m, 2H).

Scheme IIIb

Example 39

Synthesis of mono(3-benzyloxycyclohexyl) glutarate

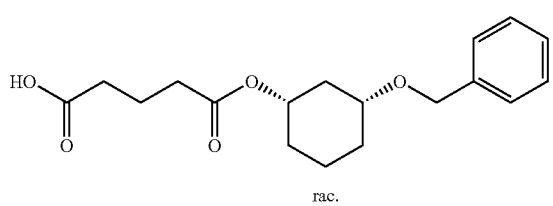

3.0 g of 3-benzyloxycyclohexan-1-ol, 2.15 g of glutaric anhydride and 3.03 g of triethylamine were stirred at 21–23° C. in 25 ml of methylene chloride. After complete conversion, the mixture was added to water, extracted, and dried over $MgSO_4$. After concentrating under reduced pressure, 4.3 g of the desired compound were obtained; $^1$H NMR ($CDCl_3$), δ=1.20–1.28 (m, 4H), 1.82 (m, 1H), 1.90–1.97 (m, 3H), 2.05 (m, 1H), 2.32–2.42 (m, 5H), 3.39 (m, 1H), 4.55 (dd, 2H), 4.69 (m, 1H), 7.25–7.33 (m, 5H), 8.7 (br., 1H).

Example 40

Stereoselective hydrolysis of mono(3-benzyloxycyclohexyl) glutarate, preparation of (1R,3S)-3-benzyloxycyclohexan-1-ol

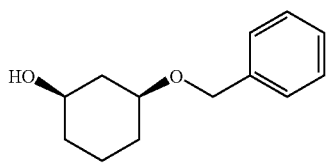

20 mg of racemic mono(3-benzyloxycyclohexyl) glutarate (from Example 39) were partitioned into 2 ml of phosphate buffer, pH 8, and 3–5 drops of DME, admixed with 3–5 mg of Novozyme 435 and stirred at 21–23° C. After approx. 50% conversion, the reaction solution was partitioned between saturated aqueous NaHCO₃ solution and ethyl acetate. The ethyl acetate phase was dried and concentrated, yield: 5 mg of (1R,3S)-3-benzyloxycyclohexan-1-ol, and the enantiomeric excess was >95% (HPLC on Chiralpak AD-H 250×4.6; 1 ml/min, 25:1:0.5 heptane/EtOH/CH₃CN+0.1% TFA).

Example 41

Synthesis of (1R,3S)-4-(3-benzyloxycyclohexyl-1-oxymethyl)-2-(4-fluoro-phenyl)oxazole

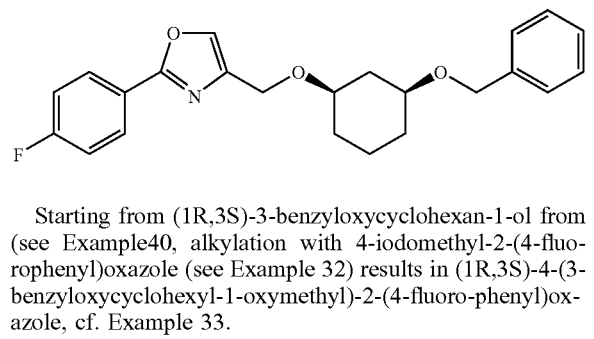

Starting from (1R,3S)-3-benzyloxycyclohexan-1-ol from (see Example 40, alkylation with 4-iodomethyl-2-(4-fluorophenyl)oxazole (see Example 32) results in (1R,3S)-4-(3-benzyloxycyclohexyl-1-oxymethyl)-2-(4-fluoro-phenyl)oxazole, cf. Example 33.

Further Examples of the Alkylation of cis-1,3-cyclohexanediol

Example 42

Synthesis of racemic methyl cis-2-(3-hydroxycyclohexyloxymethyl)-6-methylbenzoate

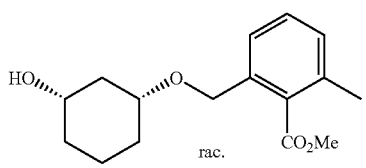

5 g (42.8 mmol) of cis-1,3-cyclohexanediol were dissolved in 50 ml of dimethoxyethane (DME), admixed at 20–23° C. with 3.36 g (30 mmol) of potassium tert-butoxide (KOtBu) and stirred. After about 30 minutes, the mixture is cooled to 5° C. and 3.7 g (approx. 50%) of methyl 2-bromomethyl-6-methylbenzoate, which may be prepared, for example, by methanolyzing the acid bromide (2-bromomethyl-6-methylbenzoyl bromide) or by brominating methyl 2,6-dimethylbenzoate, are added dropwise. The mixture is stirred at 5–10° C. for 1 h and then at 20–23° C. overnight. Water and methyl tert-butyl ether (MTBE) are added, the mixture is stirred vigorously, the phases are separated, the aqueous phase is washed once more with MTBE and the combined organic phases are concentrated under reduced pressure. The residue is chromatographed on silica gel (1:1 ethyl acetate/n-heptane). 600 mg of the desired compound are obtained as a light yellow oil, ¹H NMR (CDCl₃), δ =1.27 (m, 1H), 1.45 (m, 1H), 1.55 (m, 1H), 1.74 (m, 1H), 1.83 (m, 1H), 2.05 (m, 1H), 2.34 (s, 3H), 3.47 (m, 1H), 3.72 (m, 1H), 3.91 (s, 3H), 4.58 (dd, 2H), 7.15 (d, 1H), 7.20 (d, 2H), 7.27 (m, 1H).

Example 43

Synthesis of racemic methyl cis-2-(3-hydroxycyclohexyloxymethyl)-6-methylbenzoate

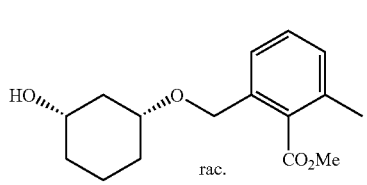

10.0 g (86 mmol) of cis-1,3-cyclohexanediol were taken up in 150 ml of methyl tert-butyl ether (MTBE), admixed at approx. 20° C. with 6.72 g (59.9 mmol) of potassium tert-butoxide (KOtBu) and stirred. After about 30 minutes, the suspension was cooled to 5° C. and admixed dropwise with 7.4 g (approx. 50%) of methyl 2-bromomethyl-6-methylbenzoate, which may be prepared, for example, by methanolyzing the acid bromide (2-bromomethyl-6-methylbenzoyl bromide) or by brominating methyl 2,6-dimethylbenzoate. The mixture was stirred at 0–5° C. for 1 h, heated to 20–23° C. and left to stir overnight. Water was added, the mixture was stirred vigorously, the phases were separated, the organic phase was washed once more with water and then the organic phase was concentrated under reduced pressure. The residue (4.6 g) was chromatographed on silica gel (1:1 ethyl acetate/n-heptane). 1.2 g of the desired compound were obtained as a light yellow oil, ¹H NMR (CDCl₃), δ =1.27 (m, 1H), 1.45 (m, 1H), 1.55 (m, 1H), 1.74 (m, 1H), 1.82 (m, 1H), 2.05 (m, 1H), 2.34 (s, 3H), 3.46 (m, 1H), 3.72 (m, 1H), 3.91 (s, 3H), 4.58 (dd, 2H), 7.15 (d, 1H), 7.20 (d, 2H), 7:27 (m, 1H).

Example 44

Synthesis of racemic methyl cis-2-(3-hydroxycyclohexyloxymethyl)-6-methylbenzoate

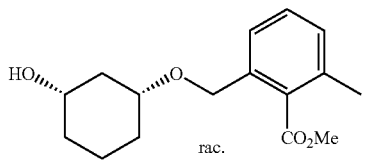

5 g (42.8 mmol) of cis-1,3-cyclohexanediol were dissolved in 40 ml of chlorobenzene and 10 ml of 1,3-dimethyl-3,4,5,6-tetrahydro-2(1H)-pyrimidinone (DMPU, dimethylpropyleneurea), admixed at 20–23° C. with 3.36 g (30 mmol) of potassium tert-butoxide (KOtBu) and stirred. After 10–15 minutes, the mixture was cooled to 15–20° C. and 3.7 g (approx. 50%) of methyl 2-bromomethyl-6-methylbenzoate were added dropwise. The mixture was stirred at 20° C. for 1.5 h and then added to water. The organic phase was removed and concentrated under reduced pressure. The residue was taken up in NMP/water and, to remove impurities, washed twice with n-heptane. Subsequently, the product was isolated by extracting twice with MTBE. The combined MTBE phases were washed with water, dried ($Na_2SO_4$) and concentrated under reduced pressure. The residue (1.2 g) was chromatographed on silica gel (1:1 ethyl acetate/n-heptane). 580 mg of the desired compound were obtained as a slightly yellow oil; $^1$H-NMR ($CDCl_3$), δ =1.27 (m, 1H), 1.45 (m, 1H), 1.55 (m, 1H), 1.74 (m, 1H), 1.83 (m, 1H), 2.05 (m, 1H), 2.34 (s, 3H), 3.47 (m, 1H), 3.72 (m, 1H), 3.91 (s, 3H), 4.58 (dd, 2H), 7.15 (d, 1H), 7.20 (d, 2H), 7.27 (m, 1H).

Further Examples of the Optical Resolution by Stereoselective Ester Formation (EF)

Example 45

Optical resolution of methyl cis-2-(3-hydroxycyclohexyloxymethyl)-6-methylbenzoate

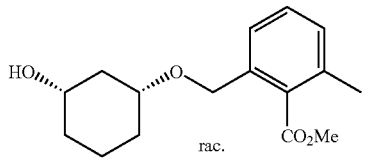

730 mg of the racemic methyl cis-2-(3-hydroxycyclohexyl-1-oxymethyl)-6-methylbenzoate are dissolved in 5 ml of methylene chloride and 2 ml of vinyl acetate, heated to 38° C. and admixed with 100 mg of Novozym 435. After approx. 5 h, the reaction was ended by filtering off the enzyme and the optical purity of the acetate formed and of the unconverted alcohol were determined by HPLC (HPLC$_{acetate}$:Chiralcel OD 250×4.6, 1 ml/min, 100:1:0.5 heptane/EtOH/$CH_3CN$; HPLC$_{alcohol}$:Chiralpak AD 250×4.6; 1 ml/min, 25:1:0.5 heptane/EtOH/$CH_3CN$+0.1% TFA). The determination of the optical purity for methyl (3S,1R)-2-(3-hydroxycyclohexyl-1-oxymethyl)-6-methylbenzoate gave 98% ee and 86% ee for the (3R,1S)-acetate.

Example 46

Optical resolution of methyl cis-2-(3-hydroxycyclohexyl-1-oxymethyl)-6-methylbenzoate

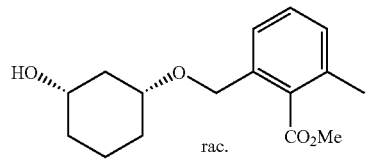

20 mg of the racemic methyl cis-2-(3-hydroxycyclohexyl-1-oxymethyl)-6-methylbenzoate were dissolved in 2 ml of chlorobenzene and 1 ml of vinyl acetate, admixed at 22–25° C. with 8 mg of Chirazyme L-2, lyo. (Roche), and stirred. After approx. 6 h, the reaction was ended by filtering off the enzyme and the optical purity of the acetate formed and of the unconverted alcohol were determined by HPLC (HPLC$_{acetate}$:Chiralcel OD 250×4.6, 1 ml/min, 100:1:0.5 heptane/EtOH/$CH_3CN$; HPLC$_{alcohol}$:Chiralpak AD 250×4.6; 1 ml/min, 25:1:0.5 heptane/EtOH/$CH_3CN$+0.1% TFA) were determined: 84% ee of methyl (3S,1R)-2-(3-hydroxycyclohexyl-1-oxymethyl)-6-methylbenzoate and 95% ee of the (3R,1S)-acetate.

Example 47

Optical resolution of methyl cis-2-(3-hydroxycyclohexyl-1-oxymethyl)-6-methylbenzoate

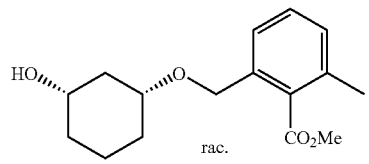

1.0 g of methyl cis-2-(3-hydroxycyclohexyl-1-oxymethyl)-6-methylbenzoate were dissolved in 10 ml of 1,2-dichloroethane and 2 ml of vinyl propionate, admixed with 25 mg of Chirazyme L-2, lyo. (Roche) and stirred at 21–24° C. for 40 h. Filtering off the enzyme, concentrating the filtrate under reduced pressure and chromatography of the residue on silica gel (1:1 ethyl acetate/n-heptane) gave 0.49 g of the (3R,1S)-propionate having 92% ee (HPLC on Chiralcel OD 250×4.6, 1 ml/min, 100:1:0.5 heptane/-EtOH/$CH_3CN$), $^1$H NMR ($CDCl_3$), δ =1.13 (t, 3H), 1.15–1.36 (m, 4H), 1.79 (m, 1H), 1.91 (m, 1H), 2.01 (m, 1H), 2.30 (q, 2H), 2.34 (s, 3H), 2.35 (m, 1H), 3.34 (m, 1H), 3.90 (s, 3H), 4.58 (dd, 2H), 4.67 (m, 1H), 7.14 (d, 1H), 7.19 (d, 1H), 7.26 (m, 1H), and also 0.3 g of the unconverted methyl (3S, 1R)-2-(3-hydroxycyclohexyl-1-oxymethyl)-6-methylbenzoate having 98% ee (HPLC on Chiralpak AD-H 250×4.6; 1 ml/min, 25:1:0.5 heptane/EtOH/$CH_3CN$+0.1% TFA), $^1$H NMR ($CDCl_3$), δ =1.27 (m, 1H), 1.45 (m, 1H), 1.55 (m, 1H), 1.74 (m, 1H), 1.83 (m, 1H), 2.05 (m, 1H), 2.34 (s, 3H), 3.47 (m, 1H), 3.72 (m, 1H), 3.91 (s, 3H), 4.58 (dd, 2H), 7.15 (d, 1H), 7.20 (d, 2H), 7.27 (m, 1H).

Example 48

Optical resolution of methyl cis-2-(3-hydroxycyclohexyl-1-oxymethyl)-6-methylbenzoate

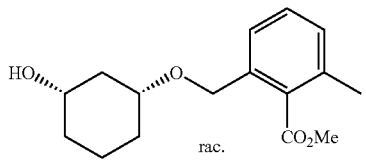

10 mg of the racemic methyl cis-2-(3-hydroxycyclohexyl-1-oxymethyl)-6-methylbenzoate were dissolved in 1 ml of vinyl acetate, admixed with approx. 4–6 mg of Lipase TL (Pseud. stutzeri, Meito Sangyo) and stirred at 22–25° C. After >50% conversion, the reaction was ended by filtering off the enzyme and the optical purity of the unconverted methyl (3S,1R)-2-(3-hydroxycyclohexyl-1-oxymethyl)-6-methylbenzoate was determined: >98% ee (HPLC on Chiralpak AD 250×4.6; 1 ml/min, 25:1:0.5 heptane/EtOH/$CH_3CN$+0.1% TFA).

Example 49

Optical resolution of methyl cis-2-(3-hydroxycyclohexyloxymethyl)-6-methylbenzoate

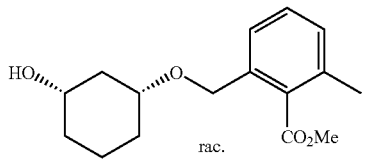

3.9 g of the racemic methyl cis-2-(3-hydroxycyclohexyl-1-oxymethyl)-6-methylbenzoate were dissolved in 25 ml of methylene chloride and 10 ml of vinyl acetate, heated to 45° C. and admixed with 250 mg of Novozym 435. After approx. 45% conversion, the reaction was ended by filtering off the enzyme and the reaction mixture was concentrated. Chromatography of the residue on silica gel (1:1 ethyl acetate/n-heptane) gave 1.9 g of the (3R,1S)-acetate (>95% ee, HPLC on Chiralcel OD 250×4.6, 1 ml/min, 100:1:0.5 heptane/EtOH/$CH_3CN$) and 1.9 g of the unconverted methyl (3S,1R)-2-(3-hydroxycyclohexyl-1-oxymethyl)-6-methylbenzoate (82% ee, HPLC on Chiralpak AD 250×4.6; 1 ml/min, 25:1:0.5 heptane/EtOH/$CH_3CN$+0.1% TFA).

Example 50

Optical resolution of methyl cis-2-(3-hydroxycyclohexyloxymethyl)-6-methylbenzoate

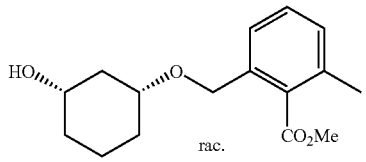

20 mg of the racemic methyl cis-2-(3-hydroxycyclohexyl-1-oxymethyl)-6-methylbenzoate were dissolved in 2 ml of toluene and 1 ml of vinyl acetate, admixed at 20–23° C. with 6–8 mg of Chirazyme L-2, lyo. (Roche), and stirred. After approx. 45% conversion, the reaction was ended by filtering off the enzyme and the optical purity of the (3R,1S)-acetate formed was determined: 94% ee (HPLC on Chiralcel OD 250×4.6, 1 ml/min, 100:1:0.5 heptane/EtOH/$CH_3CN$).

Example 51

Optical resolution of methyl cis-2-(3-hydroxycyclohexyloxymethyl)-6-methylbenzoate

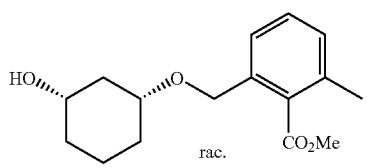

10 mg of the racemic methyl cis-2-(3-hydroxycyclohexyl-1-oxymethyl)-6-methylbenzoate were dissolved in 1 ml of vinyl acetate, admixed with approx. 4–6 mg of Lipase QL (Alcaligenes spec., Meito Sangyo) and stirred at 20–23° C. After approx. 52% conversion, the reaction was ended by filtering off the enzyme and the optical purity of the acetate formed and of the unconverted alcohol were determined, ee of the acetate: 91% (HPLC on Chiralcel OD 250×4.6, 1 ml/min, 100:1:0.5 heptane/EtOH/$CH_3CN$), ee of the methyl (3S,1R)-2-(3-hydroxycyclohexyl-1-oxymethyl)-6-methylbenzoate: >98% ee (HPLC on Chiralpak AD 250×4.6; 1 ml/min, 25:1:0.5 heptane/EtOH/$CH_3CN$+0.1% TFA).

Example 52

Optical resolution of methyl cis-2-(3-hydroxycyclohexyloxymethyl)-6-methylbenzoate

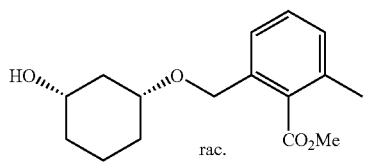

10 mg of the racemic methyl cis-2-(3-hydroxycyclohexyl-1-oxymethyl)-6-methylbenzoate were dissolved in 1 ml of vinyl acetate, admixed with approx. 4–6 mg of Lipase SL (Pseud. cepacia, Meito Sangyo) and stirred at 20–23° C. After approx. 52% conversion, the reaction was ended by filtering off the enzyme and the optical purity of the acetate formed and of the unconverted alcohol were determined, ee of the acetate: 90% (HPLC on Chiralcel OD 250×4.6, 1 ml/min, 100:1:0.5 heptane/EtOH/$CH_3CN$), ee of the methyl (3S,1R)-2-(3-hydroxycyclohexyl-1-oxymethyl)-6-methylbenzoate: >95% ee (HPLC on Chiralpak AD 250×4.6; 1 ml/min, 25:1:0.5 heptane/EtOH/$CH_3CN$+0.1% TFA).

Example 53

Optical resolution of methyl cis-2-(3-hydroxycyclo-hexyloxymethyl)-6-methylbenzoate

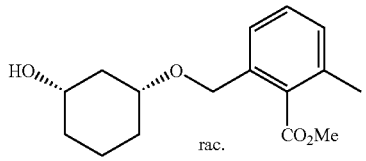
rac.

39 g of methyl cis-2-(3-hydroxycyclohexyl-1-oxymethyl)-6-methylbenzoate were dissolved in 250 ml of methylene chloride and 50 ml of vinyl acetate, heated to 45° C. and admixed with 1.0 g of Novozym 435. After 25 h, a further 0.5 g of Novozym 435 was added. After a further 6.5 hours, the enzyme was filtered off and the reaction mixture concentrated. Chromatography of the residue on 630 g of silica gel (1:1 ethyl acetate/n-heptane) gave 18.2 g of methyl (3S,1R)-2-(3-hydroxycyclohexyl-1-oxymethyl)-6-methylbenzoate (>98% ee, HPLC on Chiralpak AD-H 250×4.6; 1 ml/min, 25:1:0.5 heptane/EtOH/CH$_3$CN+0.1% TFA), $^1$H NMR (CDCl$_3$), δ =1.27 (m, 1H), 1.45 (m, 1H), 1.55 (m, 1H), 1.74 (m, 1H), 1.83 (m, 1H), 2.05 (m, 1H), 2.34 (s, 3H), 3.47 (m, 1H), 3.72 (m, 1H), 3.91 (s, 3H), 4.58 (dd, 2H), 7.15 (d, 1H), 7.20 (d, 2H), 7.27 (m, 1H).

Example 54

Optical resolution of methyl cis-2-(3-hydroxycyclo-hexyloxymethyl)-6-methylbenzoate

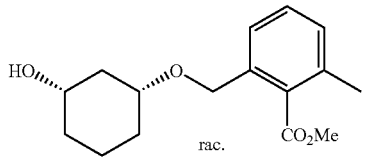
rac.

20 mg of the racemic methyl cis-2-(3-hydroxycyclohexyl-1-oxymethyl)-6-methylbenzoate were dissolved in 2 ml of THF and 1 ml of vinyl acetate, admixed at 20–23° C. with 6–8 mg of Chirazyme L-2, lyo. (Roche), and stirred. After approx. 6 h, the reaction was ended by filtering off the enzyme and the optical purity of the acetate formed and of the unconverted alcohol were determined by HPLC (HPLC$_{acetate}$:Chiralcel OD 250×4.6, 1 ml/min, 100:1:0.5 heptane/EtOH/CH$_3$CN; HPLC$_{alcohol}$:Chiralpak AD 250×4.6; 1 ml/min, 25:1:0.5 heptane/EtOH/CH$_3$CN+0.1% TFA): ee of the methyl (3S,1R)-2-(3-hydroxycyclohexyl-1-oxymethyl)-6-methylbenzoate 89% and ee of the (3R,1S)-acetate 95% and

Example 55

Optical resolution of methyl cis-2-(3-hydroxycyclo-hexyloxymethyl)-6-methylbenzoate

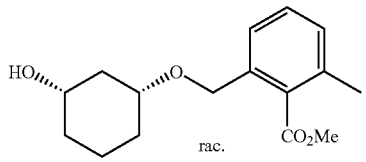
rac.

Approx. 15 mg of the racemic methyl cis-2-(3-hydroxy-cyclohexyl-1-oxymethyl)-6-methylbenzoate were dissolved in 2 ml of tert-butanol and 1 ml of vinyl acetate, admixed at 20–23° C. with approx. 6 mg of Novozym 435 and stirred. After approx. 24 h, the reaction was ended by filtering off the enzyme and the optical purity of the acetate formed and of the unconverted alcohol were determined by HPLC: (3R, 1S)-acetate 91% ee (HPLC: Chiralcel OD 250×4.6, 1 ml/min, 100:1:0.5 heptane/EtOH/CH$_3$CN), methyl (3S,1R)-2-(3-hydroxycyclohexyl-1-oxymethyl)-6-methylbenzoate 96% ee (HPLC: Chiralpak AD 250×4.6; 1 ml/min, 25:1:0.5 heptane/EtOH/CH$_3$CN+0.1% TFA).

Example 56

Optical resolution of methyl cis-2-(3-hydroxycyclo-hexyloxymethyl)-6-methylbenzoate

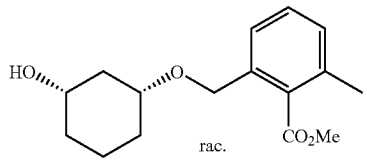
rac.

10 mg of the racemic methyl cis-2-(3-hydroxycyclohexyl-1-oxymethyl)-6-methylbenzoate were dissolved in 1 ml of vinyl acetate, admixed with approx. 4–6 mg of Lipase TL (Pseud. stutzeri, Meito Sangyo) and stirred at 20–23° C. After >50% conversion, the reaction was ended by filtering off the enzyme and the optical purity of the unconverted alcohol was determined: methyl (3S,1R)-2-(3-hydroxycyclohexyl-1-oxymethyl)-6-methylbenzoate >98% ee (HPLC on Chiralpak AD 250×4.6; 1 ml/min, 25:1:0.5 heptane/EtOH/CH$_3$CN+0.1% TFA).

Example 57

Optical resolution of cis-3-benzyloxycyclohexan-1-ol

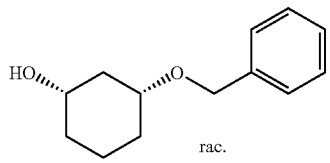
rac.

35–40 mg of racemic cis-3-benzyloxycyclohexan-1-ol were dissolved in 0.5–1 ml of vinyl acetate and 2–3 ml of methylene chloride, admixed with approx. 8–10 mg of Novozym 435 and stirred at 22–25° C. After 4 days, the reaction was ended by filtering off the enzyme. The optical purity of the alcohol, (1S,3R)-3-benzyloxycyclohexan-1-ol, was >98% ee (HPLC on Chiralpak AD-H 250×4.6; 1 ml/min, 25:1:0.5 heptane/EtOH.CH$_3$CN+0.1% TFA), and the ee of the (1R,3S)-acetate was 82% (HPLC on Chiralcel OD 250×4.6; 1 ml/min, 100:1:0.5 heptane/EtOH/CH$_3$CN).

Example 58

Optical resolution of
cis-3-benzyloxycyclohexan-1-ol

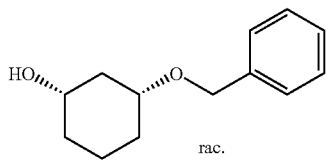

rac.

10 mg of the racemic cis-3-benzyloxycyclohexan-1-ol were dissolved in 1 ml of vinyl acetate and 3 ml of THF, admixed with approx. 5 mg of Lipase L-10 and stirred at 22–25° C. After ≧50% conversion, the reaction was ended by filtering off the enzyme. The optical purity of (1S,3R)-3-benzyloxycyclohexan-1-ol was ≧90% ee (HPLC on Chiralpak AD-H 250×4.6; 1 ml/min, 25:1:0.5 heptane/EtOH/CH$_3$CN+0.1% TFA).

Example 59

Optical resolution of
cis-3-benzyloxycyclohexan-1-ol

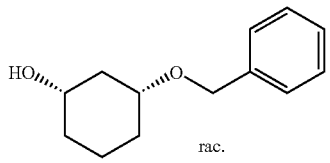

rac.

10 mg of the racemic cis-3-benzyloxycyclohexan-1-ol were dissolved in 1 ml of vinyl acetate and 3 ml of chlorobenzene, admixed with 10 mg of Novozym 435 and stirred at 22–25° C. After 4 hours, the reaction was ended by filtering off the enzyme. The optical purity of (1S,3R)-3-benzyloxycyclohexanol was 68% ee (HPLC on Chiralpak AD-H 250×4.6, 1 ml/min, 25:1:0.5 heptane/EtOH/CH$_3$CN+0.1% TFA), and the ee of the enantiomeric acetate was 95% (HPLC on Chiralcel OD 250×4.6; 1 ml/min, 100:1:0.5 heptane/EtOH/CH$_3$CN).

Example 60

Optical resolution of
cis-3-benzyloxycyclohexan-1-ol

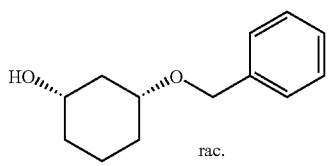

rac.

10 mg of the racemic cis-3-benzyloxycyclohexan-1-ol were dissolved in 1 ml of vinyl acetate and 3 ml of cyclohexane, admixed with approx. 5 mg of Lipase QL and stirred at 22–25° C. After 24 hours, the reaction was ended by filtering off the enzyme. The optical purity of (1S,3R)-3-benzyloxycyclohexan-1-ol was 94% ee (HPLC on Chiralpak AD-H 250×4.6; 1 ml/min, 25:1:0.5 heptane/EtOH/CH$_3$CN+0.1% TFA).

Example 61

Optical resolution of
cis-3-benzyloxycyclohexan-1-ol

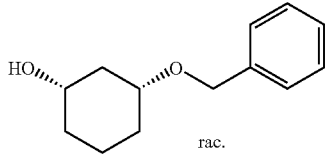

rac.

10 mg of the racemic cis-3-benzyloxycyclohexan-1-ol were dissolved in 1 ml of vinyl acetate and 3 ml of toluene, admixed with 10 mg of Novozym 435 and stirred at 22–25° C. After 4 hours, the reaction was ended by filtering off the enzyme. The optical purity of (1S,3R)-3-benzyloxycyclohexan-1-ol was 70% ee (HPLC on Chiralpak AD-H 250×4.6, 1 ml/min, 25:1:0.5 heptane/EtOH/CH$_3$CN+0.1% TFA), and the ee of the (1R,3S)-acetate was 95% (HPLC on Chiralcel OD 250×4.6; 1 ml/min, 100:1:0.5 heptane/EtOH/CH$_3$CN).

Example 62

Optical resolution of
cis-3-benzyloxycyclohexan-1-ol

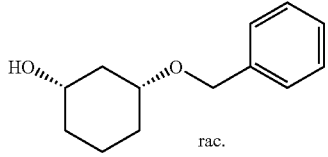

rac.

10 mg of the racemic cis-3-benzyloxycyclohexan-1-ol were dissolved in 1 ml of vinyl acetate and 3 ml of cyclohexane, admixed with approx. 10 mg of Novozym 435 and stirred at 22–25° C. After approx. 4 hours, the reaction was ended by filtering off the enzyme. The optical purity of (1S,3R)-3-benzyloxycyclohexan-1-ol was 95% ee (HPLC on Chiralpak AD-H 250×4.6, 1 ml/min, 25:1:0.5 heptane/EtOH/CH$_3$CN+0.1% TFA), and the ee of the (1R,3S)-acetate was 90% (HPLC on Chiralcel OD 250×4.6; 1 ml/min, 100:1:0.5 heptane/EtOH/CH$_3$CN).

Example 63

Optical resolution of
cis-3-benzyloxycyclohexan-1-ol

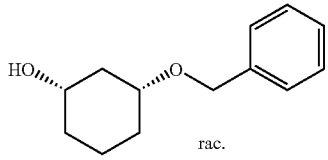

rac.

10 mg of the racemic cis-3-benzyloxycyclohexan-1-ol were dissolved in 1 ml of vinyl acetate and 3 ml of cyclohexane, admixed with approx. 5 mg of Lipase L-10 and stirred at 22–25° C. After 24 hours, the reaction was ended by filtering off the enzyme. The optical purity of (1S,3R)-3-benzyloxycyclohexan-1-ol was >95% ee (HPLC on Chiralpak AD-H 250×4.6; 1 ml/min, 25:1:0.5 heptane/EtOH/CH$_3$CN+0.1% TFA).

Example 64

Optical resolution of cis-3-benzyloxycyclohexan-1-ol

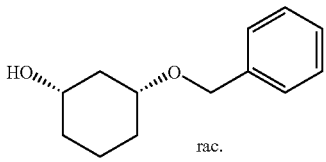

Approx. 10 mg of the racemic cis-3-benzyloxycyclohexan-1-ol were dissolved in 1 ml of vinyl acetate and 3 ml of THF, admixed with 10 mg of Novozym 435 and stirred at 22–25° C. After 4 hours, the reaction was ended by filtering off the enzyme. The optical purity of (1S,3R)-3-benzyloxycyclohexanol was 73% ee (HPLC on Chiralpak AD-H 250×4.6; 1 ml/min, 25:1:0.5 heptane/EtOH/CH$_3$CN+0.1% TFA), and the ee of the (1R,3S)-acetate was 94% (HPLC on Chiralcel OD 250×4.6; 1 ml/min, 100:1:0.5 heptane/EtOH/CH$_3$CN).

Example 65

Optical resolution of cis-3-benzyloxycyclohexan-1-ol

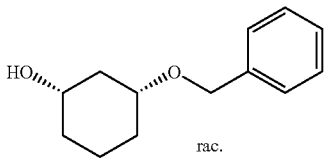

10 mg of the racemic cis-3-benzyloxycyclohexan-1-ol were dissolved in 1 ml of vinyl acetate and 3 ml of chlorobenzene, admixed with approx. 5 mg of Lipase L-10 and stirred at 22–25° C. After ≧50% conversion, the reaction was ended by filtering off the enzyme. The optical purity of (1S,3R)-3-benzyloxycyclohexan-1-ol was ≧92% ee (HPLC on Chiralpak AD-H 250×4.6; 1 ml/min, 25:1:0.5 heptane/EtOH/CH$_3$CN+0.1% TFA).

Example 66

Optical resolution of cis-3-benzyloxycyclohexan-1-ol

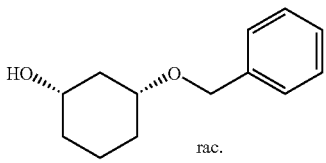

Approx. 10 mg of the racemic cis-3-benzyloxycyclohexan-1-ol were dissolved in 1 ml of vinyl acetate and 3 ml of ethyl acetate, admixed with approx. 10 mg of Novozym 435 and stirred at 22–25° C. After 4 hours, the reaction was ended by filtering off the enzyme. The optical purity of (1S,3R)-3-benzyloxycyclohexan-1-ol was 77% ee (HPLC on Chiralpak AD-H 250×4.6; 1 ml/min, 25:1:0.5 heptane/EtOH/CH$_3$CN+0.1% TFA), and the ee of the (1R,3S)-acetate was 93% (HPLC on Chiralcel OD 250×4.6; 1 ml/min, 100:1:0.5 heptane/EtOH/CH$_3$CN).

Example 67

Optical resolution of cis-3-benzyloxycyclohexan-1-ol

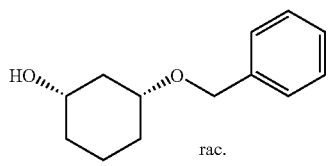

10 mg of the racemic cis-3-benzyloxycyclohexan-1-ol were dissolved in 1 ml of vinyl acetate and 3 ml of chlorobenzene, admixed with approx. 5 mg of Lipase SL and stirred at 22–25° C. After ≧50% conversion, the reaction was ended by filtering off the enzyme. The optical purity of (1S,3R)-3-benzyloxycyclohexan-1-ol was ≧87% ee (HPLC on Chiralpak AD-H 250×4.6; 1 ml/min, 25:1:0.5 heptane/EtOH/CH$_3$CN+0.1% TFA).

Example 68

Optical resolution of cis-3-benzyloxycyclohexan-1-ol

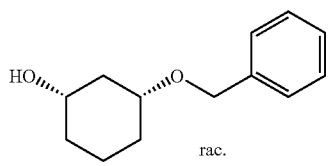

10 mg of the racemic cis-3-benzyloxycyclohexan-1-ol were dissolved in 1 ml of vinyl acetate and 3 ml of diisopropyl ether, admixed with 10 mg of Novozym 435 and stirred at 22–25° C. After 4 hours, the reaction was ended by filtering off the enzyme. The optical purity of (1S,3R)-3-benzyloxy-cyclohexan-1-ol was 90% ee (HPLC on Chiralpak AD-H 250×4.6; 1 ml/min, 25:1:0.5 heptane/EtOH/CH$_3$CN+0.1% TFA), and the ee of the (1R,3S)-acetate was 90% (HPLC on Chiralcel OD 250×4.6; 1 ml/min, 100:1:0.5 heptane/EtOH/CH$_3$CN).

Example 69

Optical resolution of cis-3-benzyloxycyclohexan-1-ol

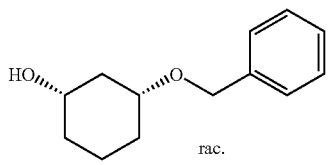

rac.

10 mg of the racemic cis-3-benzyloxycyclohexan-1-ol were dissolved in 1 ml of vinyl acetate and 3 ml of MTBE, admixed with 10 mg of Novozym 435 and stirred at 22–25° C. After 4 hours, the reaction was ended by filtering off the enzyme. The optical purity of (1S,3R)-3-benzyloxy-cyclohexan-1-ol was 93% ee (HPLC on Chiralpak AD-H 250×4.6; 1 ml/min, 25:1:0.5 heptane/EtOH/$CH_3CN$+0.1% TFA), and the ee of the (1R,3S)-acetate was 89% (HPLC on Chiralcel OD 250×4.6; 1 ml/min, 100:1:0.5 heptane/EtOH/$CH_3CN$).

Example 70

Optical resolution of cis-3-benzyloxycyclohexan-1-ol

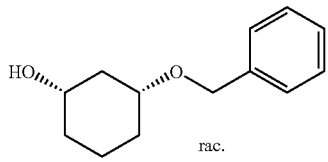

rac.

10 mg of the racemic cis-3-benzyloxycyclohexan-1-ol were dissolved in 1 ml of vinyl acetate and 3 ml of cyclohexane, admixed with approx. 5 mg of Lipase SL and stirred at 22–25° C. After 24 hours, the reaction was ended by filtering off the enzyme. The optical purity of (1S,3R)-3-benzyloxy-cyclohexan-1-ol was ≧90% ee (HPLC on Chiralpak AD-H 250×4.6; 1 ml/min, 25:1:0.5 heptane/EtOH/$CH_3CN$+0.1% TFA).

Example 71

Optical resolution of cis-3-benzyloxycyclohexan-1-ol

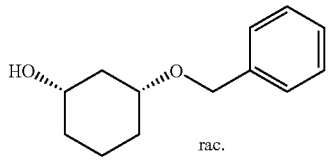

rac.

27 mg of racemic cis-3-benzyloxycyclohexan-1-ol were dissolved in 3 ml of methylene chloride, admixed with 65 mg of isovaleric anhydride and with 11 mg of Novozyme 435 and stirred at 22–25° C. After 45–50% conversion, the reaction was ended by filtering off the enzyme. The optical purity of (1S,3R)-3-benzyloxycyclohexan-1-ol was 87% ee (HPLC on Chiralpak AD-H 250×4.6; 1 ml/min, 25:1:0.5 heptane/EtOH/$CH_3CN$+0.1% TFA), and the enantiomeric excess of the (1R,3S)-isovaleric acid derivative was >95% (HPLC on Chiralcel OD 250×4.6; 1 ml/min, 100:1:0.5 heptane/EtOH/$CH_3CN$).

Example 72

Optical resolution of cis-3-benzyloxycyclohexan-1-ol

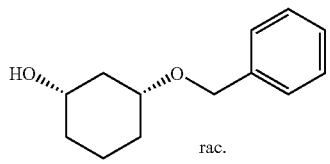

rac.

200 mg of the racemic cis-3-benzyloxycyclohexan-1-ol were dissolved in 3 ml of chlorobenzene, admixed with 100 mg of succinic anhydride and 10 mg of Chirazyme L-2, lyo., and stirred at 25–27° C. After 29 hours, the reaction was ended by filtering off the enzyme. A sample which had been concentrated by evaporation was used to determine the optical purity both of the unconverted substrate and of the acylation product formed. The optical purity of (1S,3R)-3-benzyloxycyclohexan-1-ol was >98% ee (HPLC on Chiralpak AD-H 250×4.6; 1 ml/min, 25:1:0.5 heptane/EtOH/$CH_3CN$+0.1% TFA), and the optical purity of the succinic acid derivative was 94% ee (HPLC on Chiralcel OD 250×4.6; 1 ml/min, 25:1:0.5 heptane/EtOH/$CH_3CN$+0.1% TFA).

Example 73

Optical resolution of cis-3-benzyloxycyclohexan-1-ol

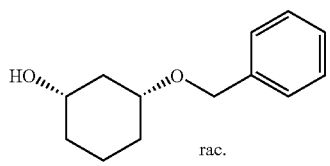

rac.

200 mg of the racemic cis-3-benzyloxycyclohexan-1-ol were dissolved in 3 ml of DME, admixed with 100 mg of succinic anhydride and 10 mg of Chirazyme L-2, lyo., and stirred at 25–27° C. After 29 hours, the reaction was ended by filtering off the enzyme. A sample which had been concentrated by evaporation was used to determine the optical purity both of the unconverted substrate and of the acylation product formed. The optical purity of (1S,3R)-3-benzyloxycyclohexan-1-ol was >95% ee (HPLC on Chiralpak AD-H 250×4.6; 1 ml/min, 25:1:0.5 heptane/EtOH/$CH_3CN$+0.1% TFA), and the optical purity of the succinic acid derivative was >97% ee (HPLC on Chiralcel OD 250×4.6; 1 ml/min, 25:1:0.5 heptane/EtOH/$CH_3CN$+0.1% TFA).

Example 74

Optical resolution of
cis-3-benzyloxycyclohexan-1-ol

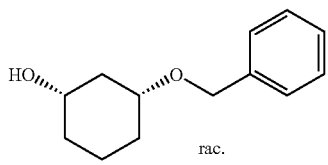
rac.

200 mg of the racemic cis-3-benzyloxycyclohexan-1-ol were dissolved in 3 ml of THF, admixed with 100 mg of succinic anhydride and 10 mg of Chirazyme L-2, lyo., and stirred at 25–27° C. After 29 hours, the reaction was ended by filtering off the enzyme. A sample which had been concentrated by evaporation was used to determine the optical purity both of the unconverted substrate and of the acylation product formed. The optical purity of (1S,3R)-3-benzyloxycyclohexan-1-ol was 84% ee (HPLC on Chiralpak AD-H 250×4.6; 1 ml/min, 25:1:0.5 heptane/EtOH/CH$_3$CN+ 0.1% TFA), and the optical purity of the succinic acid derivative was >95% ee (HPLC on Chiralcel OD 250×4.6; 1 ml/min, 25:1:0.5 heptane/EtOH/CH$_3$CN+0.1% TFA).

Example 75

Optical resolution of
cis-3-benzyloxycyclohexan-1-ol

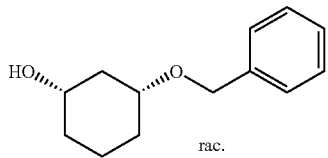
rac.

200 mg of the racemic cis-3-benzyloxycyclohexan-1-ol were dissolved in 3 ml of methylene chloride, admixed with 100 mg of succinic anhydride and 10 mg of Chirazyme L-2, lyo., and stirred at 25–27° C. After 29 hours, the reaction was ended by filtering off the enzyme. A sample which had been concentrated by evaporation was used to determine the optical purity both of the unconverted substrate and of the acylation product formed. The optical purity of (1S,3R)-3-benzyloxycyclohexan-1-ol was >98% ee (HPLC on Chiralpak AD-H 250×4.6; 1 ml/min, 25:1:0.5 heptane/EtOH/CH$_3$CN+0.1% TFA), and the optical purity of the succinic acid derivative was 88% ee (HPLC on Chiralcel OD 250×4.6; 1 ml/min, 25:1:0.5 heptane/EtOH/CH$_3$CN+0.1% TFA).

Example 76

Optical resolution of
cis-3-benzyloxycyclohexan-1-ol

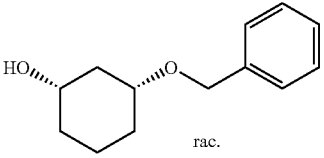
rac.

200 mg of the racemic cis-3-benzyloxycyclohexan-1-ol were dissolved in 3 ml of acetone, admixed with 100 mg of succinic anhydride and 10 mg of Chirazyme L-2, lyo., and stirred at 25–27° C. After 29 hours, the reaction was ended by filtering off the enzyme. A sample which had been concentrated by evaporation was used to determine the optical purity both of the unconverted substrate and of the acylation product formed. The optical purity of (1S,3R)-3-benzyloxycyclohexan-1-ol was >99% ee (HPLC on Chiralpak AD-H 250×4.6; 1 ml/min, 25:1:0.5 heptane/EtOH/CH$_3$CN+0.1% TFA), and the optical purity of the succinic acid derivative was 78% ee (HPLC on Chiralcel OD 250×4.6; 1 ml/min, 25:1:0.5 heptane/EtOH/CH$_3$CN+0.1% TFA).

Example 77

Optical resolution of
cis-3-benzyloxycyclohexan-1-ol, separation of
alcohol and succinic acid derivative

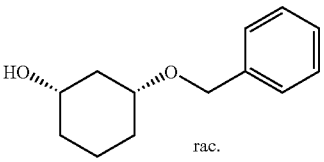
rac.

8.15 g (39.5 mmol) of the racemic cis-3-benzyloxycyclohexan-1-ol were dissolved in 120 ml of THF, admixed with 3.9 g (39.0 mmol) of succinic anhydride and 390 mg of Chirazyme L-2, lyo., and stirred at 22–25° C. After approx. 40% conversion, the reaction was ended by filtering off the enzyme. The filtrate was concentrated under reduced pressure. The residue was taken up with tBuOMe and extracted intensively three times with in each case 100 ml of sat. aqueous NaHCO$_3$ solution. The organic phase was dried (MgSO$_4$) and concentrated under reduced pressure; yield: 4.4 g; the optical purity of (1S,3R)-3-benzyloxycyclohexan-1-ol was 70% ee (HPLC on Chiralpak AD-H 250×4.6; 1 ml/min, 25:1:0.5 heptane/EtOH/CH$_3$CN+0.1% TFA). The optical purity of the succinic acid derivative dissolved in the combined aqueous phases was >99% ee (HPLC on Chiralcel OD 250×4.6; 1 ml/min, 25:1:0.5 heptane/EtOH/CH$_3$CN+ 0.1% TFA).

By treating with conc. sodium hydroxide solution, the aqueous solution of the succinic acid derivative was hydrolyzed chemically. The (1R,3S)-3-benzyloxycyclohexan-1-ol formed was extracted with tBuOMe; yield: 2.9 g.

Example 78

Optical resolution of cis-3-benzyloxycyclohexan-1-ol, separation of alcohol and succinic acid derivative

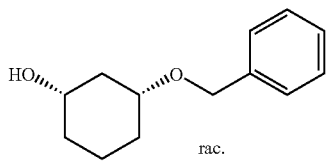
rac.

5.06 g (24.5 mmol) of the racemic cis-3-benzyloxycyclohexan-1-ol were dissolved in 75 ml of THF, admixed with 2.52 g (25.2 mmol) of succinic anhydride and 3.1 g of Novozym 435, and stirred at 22–25° C. After 28.5 h, the reaction was ended by filtering off the enzyme. The filtrate was concentrated down to approx. 15 ml under reduced pressure. The residue was admixed with 30 ml of water and the remaining THF was distilled off under reduced pressure. 15 ml of saturated aqueous $NaHCO_3$ solution, 15 ml of water and 30 ml of methylene chloride were added and the mixture was stirred intensively for 15–30 min. After phase separation, the organic phase was extracted first with 90 ml of saturated aqueous $NaHCO_3$ solution and 150 ml of water, and then with 15 ml of saturated aqueous $NaHCO_3$ solution and 30 ml of water, and washed twice with 20 ml of water. The organic phase was dried ($MgSO_4$) and concentrated under reduced pressure; yield: 2.52 g (50%), $[\alpha]_D^{20}+12.1°$ (c=1.0, MeOH); the optical purity of (1S,3R)-3-benzyloxycyclohexan-1-ol was >99% ee (HPLC on Chiralpak AD-H 250×4.6; 1 ml/min, 25:1:0.5 heptane/EtOH/$CH_3CN$+0.1% TFA).

The combined aqueous phases were admixed with 20 ml of (glacial) acetic acid and extracted twice with 20 ml of methylene chloride. The organic phase was dried ($MgSO_4$) and concentrated; yield: 3.55 g (47%) of the succinic acid derivative; the optical purity was >99% ee (HPLC on Chiralcel OD 250×4.6; 1 ml/min, 25:1:0.5 heptane/EtOH/$CH_3CN$+0.1% TFA); $^1H$ NMR ($CDCl_3$) δ : 1.2–1.43 (m, 4H), 1.82 (m, 1H), 1.93 (m, 1H), 2.04 (m, 1H), 2.40 (m, 1H), 2.58–2.70 (m, 4H), 3.39 (m, 1H), 4.54 (m, 2H), 4.71 (m, 1H); 7.23–7.36 (m, 5H).

Example 79

Preparation of racemic cis-3-(tert-butyldimethylsilanyloxy)cyclohexanol

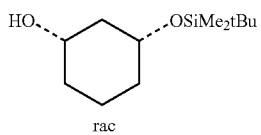
rac

TBDMSCl (28.62 g, 1.1 eq) was added slowly to a solution, cooled to 10° C., of 1,3-cyclohexanediol (20.05 g, 0.173 mol), $Et_3N$ (28.79 ml, 1.2 eq) and DMAP (0.844 g, 0.04 eq) in $CH_2Cl_2$ (600 ml). After stirring at 20–23° C. for 18 hours, the reaction mixture was washed with $H_2O$ (2×100 ml). The organic phase was washed with sat. $NH_4Cl$ (2×100 ml), dried over $MgSO_4$ and concentrated under reduced pressure. Chromatography on silica gel, (20:1 n-heptane/ethyl acetate) gave 18.77 g (47%) of the desired monsilyl ether; $^1H$ NMR ($CDCl_3$) δ : 0.0–0.1 (m, 6H), 0.8–0.9 (m, 9H), 1.2–2.0 (m, 8H), 3.2 (s, br., 1H), 3.8 (m, 1H), 3.95 (m, 1H).

Example 80

Preparation of cis-(1S, 3R)-3-(tert-butyldimethylsilanyloxy)cyclohexanol

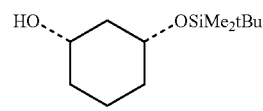

770 mg of racemic cis-3-(tert-butyldimethylsilanyloxy)cyclohexanol were dissolved in 10 ml of acetone, admixed with 0.36 ml of vinyl acetate and 400 mg of Novozym 435 and stirred at 21–24° C. After 47 h (approx. 50% conversion), the reaction was ended by filtering off the enzyme and the solution was concentrated by evaporation under reduced pressure. Chromatography of a portion of silica gel (3:1 n-heptane/ethyl acetate) gave (1S,3R)-3-(tert-butyldimethylsilanyloxy)cyclohexanol having $[\alpha]_D^{20}+12.8°$ (c=1.0, MeOH).

What is claimed is:

1. A process for preparing a chiral, nonracemic compound of the formula I

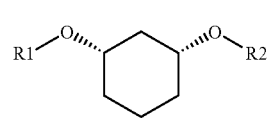
(I)

where:
$R^1$ is

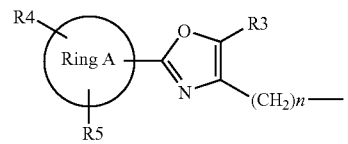

where:
ring A is phenyl, 5–12 membered heteroaromatic ring which may contain from one to four heteroatoms from the group of N, O and S, 8 to 14 membered aromatic ring, ($C_3$–$C_8$)-cycloalkyl;
$R^3$ is H, F, Cl, Br, OH, $NO_2$, $CF_3$, $OCF_3$, ($C_1$–$C_6$)-alkyl, ($C_3$–$C_8$)-cycloalkyl, phenyl;
$R^4$, $R^5$ are H, F, Cl, Br, OH, $NO_2$, $CF_3$, $OCF_3$, $OCF_2H$, $OCF_2$—$CF_3$, $OCF_2$—$CHF_2$, $SCF_3$, O-phenyl, ($C_1$–$C_6$)-alkyl, O—($C_1$–$C_6$)-alkyl, O—($C_1$–$C_6$)-alkyl-O—($C_1$–$C_3$)-alkyl;
n is from 1 to 3; and
$R^2$ is ($C_1$–$C_8$)-alkyl where one or more $CH_2$ groups in the alkyl groups may be replaced by O, CO, S, SO or $SO_2$, and alkyl may be one to trisubstituted by F, Cl, Br, $CF_3$, ON, $NO_2$, NHAc, NHBoc, NH—CO—$C(CH_3)_3$, hydroxyl, $OCF_3$, $O-(C_1-C_6)$-alkyl, COOH, CO-benzoxy, $CO-O(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, $NH-CO-C(CH_3)_3$, hydroxyl, $OCF_3$, $O-(C_1-C_6)$-alkyl, COOH, CO-benzoxy, $CO-O(C_1-C_6)$-alkyl, $(C_1-C_6)$-alkyl, $O-(C_1-C_6)$-alkyl or tetrazole;

which comprises a) alkylation (alk-R2)

reacting cis-1,3-cyclohexanediol of the formula (II)

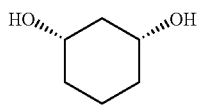
(II)

with a compound of the formula (III)

$X^1-R^2$ (III)

where $R^2$ is as defined above and
$X^1$ is Cl, Br, I, OMs, OTs, OTf;
in the presence of bases in a suitable solvent to give a racemic compound of the formula (IV)

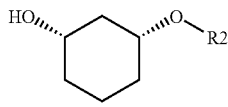
(IV)

where $R^2$ is as defined above;

b1) enzymatic ester formation (EF)+separation (S)

subjecting the resulting compounds of the formula (IV) to stereoselective enzymatic ester formation (EF), in which the alcohols are admixed with an acyl donor and the enzyme in an organic solvent and the resulting mixture is stirred at −20 to 80° C. and, after the reaction has ended, one stereoisomer is present as an ester of the formula (V)

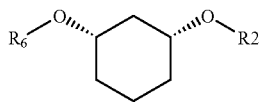
(V)

where
$R^6$ is $C(=O)-(C_1-C_{16})$-alkyl, $C(=O)-(C_2-C_{16})$-alkenyl, $C(=O)-(C_3-C_{16})$-alkynyl, $C(=O)-(C_3-C_{16})$-cycloalkyl, where one or more carbon atoms may be replaced by oxygen atoms and be substituted by 1–3 substituents from the group of F, Cl, Br, $CF_3$, CN, $NO_2$, hydroxyl, methoxy, ethoxy, phenyl and $CO-O(C_1-C_4)$-alkyl, $CO-O(C_2-C_4)$-alkenyl, which may in turn be substituted by 1–3 substituents from the group of F, Cl, Br, $CF_3$, and
$R^2$ is as defined above, and the other stereoisomer is present unchanged as the alcohol of the formula (IV), and are therefore separated from each other by utilizing their different chemical or physicochemical properties (separation S) or b2) enzymatic ester hydrolysis [=chemical esterification (CE)+enzymatic hydrolysis (EH)]+separation (S)

subjecting the resulting compound of the formula (IV) to a stereoselective enzymatic ester hydrolysis, in which the racemic alcohol is initially converted by chemical esterification (CE), for example by means of acid chloride $R^6-Cl$ or acid anhydride $R^6-O-R^6$, in the presence of bases, to the racemic ester of the formula (V)

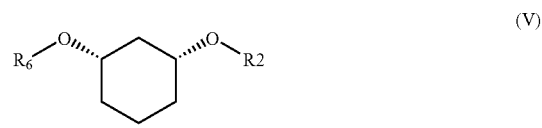
(V)

where $R^6$ and $R^2$ are each as defined above, which, to carry out the stereoselective enzymatic ester hydrolysis (EH), is then taken up in homogeneous or heterogenous, aqueous, aqueous-organic or organic medium, and reacted, in the presence of an enzyme in the case of hydrolysis with water and in the case of alcoholysis with an alcohol, at a temperature of 10–80° C., and after the reaction has ended, one stereoisomer is present as the alcohol of the formula (IV) and the other is present unchanged as the ester of the formula (V) and can thus be separated from each other as described under b1), and the enantiomer of the formula (IV) occurring as an alcohol is further processed as described under d), or c) chemical hydrolysis (CH)

hydrolyzing the enantiomer of the formula (V) occurring as an ester to the chemically enantiomeric alcohol by known methods and d) alkylation (alk-$R^1$)

reacting further with a compound of the formula (VI)

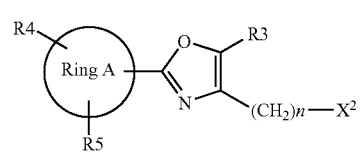
(VI)

where
ring A, $R^3$, $R^4$, $R^5$ and n are each as defined above and
$X^2$ is Cl, Br, I, OTs, OMs, OTf;
in the presence of bases in a suitable solvent to give the compound of the formula (I).

2. The process of claim 1, wherein compounds of the formula (III)

$X^1-R^2$ (III)

are used where
$X^1$ is Cl, Br, I, OMs or OTs.

3. The process of claim 2, wherein compounds of the formula (III)

$X^1-R^2$ (III)

are used where
$X^1$ is Cl, Br or I.

4. The process of claim 1, wherein a compound of the formula (I)

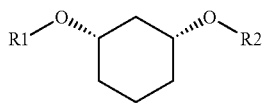

is prepared where:
R$^1$ is

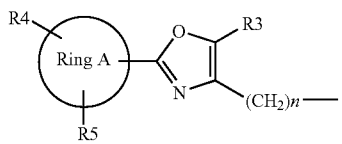

where
ring A is phenyl, 5–12 membered heteroaromatic ring which may contain from one or more heteroatoms from the group of N, O and S, fused/bicyclic 8 to 14 membered aromatic ring, (C$_3$–C$_8$)-cycloalkyl;
R$^3$ is H, CF$_3$, (C$_1$–C$_6$)-alkyl, (C$_3$–C$_8$)-cycloalkyl, phenyl;
R$^4$, R$^5$ are H, F, Br, CF$_3$, OCF$_3$, (C$_1$–C$_6$)-alkyl, O—(C$_1$–C$_6$)-alkyl;
n is from 1 to 2 and
R$^2$ is (C$_1$–C$_8$)-alkyl where one or more CH$_2$ groups in the alkyl groups may be replaced by O, CO, S, SO or SO$_2$, and alkyl may be one to trisubstituted by F, Cl, Br, CF$_3$, CN, NO$_2$, NHAc, NHBoc, NH—CO—C(CH$_3$)$_3$, hydroxyl, OCF$_3$, O—(C$_1$–C$_6$)-alkyl, COOH, CO-benzoxy, CO—O(C$_1$–C$_6$)-alkyl, tetrazole, thiazolidin-2,4-dione, indole and (C$_6$–C$_{10}$)-aryl, were thiazolidin-2,4-dione and aryl in turn maybe substituted by F, Cl, Br, CF$_3$, CN, NO$_2$, NHAc, NHTs, NHBoc, NHCbz, NH—CO—C(CH$_3$)$_3$, hydroxyl, OCF$_3$, O—(C$_1$–C$_6$)-alkyl, COOH, CO-benzoxy, CO—O(C$_1$–C$_6$)-alkyl, (C$_1$–C$_6$)-alkyl, O—(C$_1$–C$_6$)-alkyl or tetrazole.

5. The process of claim 4, wherein a compound of the formula (I)

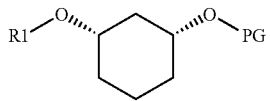

is prepared where:
R$^1$ is

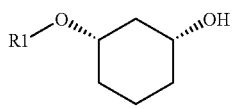

where
ring A is phenyl;
R$^3$ is (C$_1$–C$_4$)-alkyl;
R$^4$, R$^5$ are H, (C$_1$–C$_4$)-alkyl, O—(C$_1$–C$_4$)-alkyl;
n is 1 and R$^2$ is (C$_1$–C$_8$)-alkyl where one or more CH$_2$ groups in the alkyl groups may be replaced by O, CO, S, SO or SO$_2$, and alkyl may be one to trisubstituted by F, Cl, Br, CF$_3$, CN, NO$_2$, NHAc, NHBoc, NH—CO—C(CH$_3$)$_3$, hydroxyl, OCF$_3$, O—(C$_1$–C$_6$)-alkyl, COOH, CO-benzoxy, CO—O(C$_1$–C$_6$)-alkyl, tetrazole, thiazolidin-2,4-dione, indole and (C$_6$–C$_{10}$)-aryl, where thiazolidin-2,4-dione and aryl in turn maybe substituted by F, Cl, Br, CF$_3$, CN, NO$_2$, NHAc, NHTs, NHBoc, NHCbz, NH—CO—C(CH$_3$)$_3$, hydroxyl, OCF$_3$, O—(C$_1$–C$_6$)-alkyl, COOH, CO-benzoxy, CO—O(C$_1$–C$_6$)-alkyl, (C$_1$–C$_6$)-alkyl, O—(C$_1$–C$_6$)-alkyl or tetrazole.

6. The process as claimed in any of claims 1, 2, 3, 4 or 5, wherein the compound of the formula (I) is (1R,3S)-2-{3-[2-(3-methoxyphenyl)-5-methyloxazol-4-ylmethoxy]cyclohexyl-1-oxymethyl}-6-methylbenzoic acid.

7. The process as claimed in any of claims 1, 2, 3, 4 or 5, wherein the compound of the formula (I) is (1R,3S)-2-{3-[2-(4-methylphenyl)-5-methyloxazol-4-yl-methoxy]cyclohexyl-1-oxymethyl}-6-methylbenzoic acid.

8. A process for preparing a chiral, nonracemic compound of the formula I

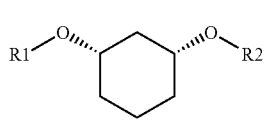

where:
R$^1$ is

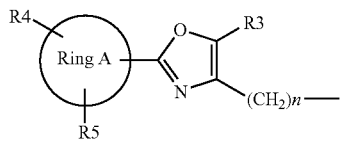

where:
ring A is phenyl, 5–12 membered heteroaromatic ring which may contain from one to four heteroatoms from the group of N, O and S, 8 to 14 membered aromatic ring, (C$_3$–C$_8$)-cycloalkyl;
R$^3$ is H, F, Cl, Br, OH, NO$_2$, CF$_3$, OCF$_3$, (C$_1$–C$_6$)-alkyl, (C$_3$–C$_8$)-cycloalkyl, phenyl;
R$^4$, R$^5$ are H, F, Cl, Br, OH, NO$_2$, CF$_3$, OCF$_3$, OCF$_2$H, OCF$_2$—CF$_3$, OCF$_2$—CHF$_2$, SCF$_3$, O—phenyl, (C$_1$–C$_6$)-alkyl, O—(C$_1$–C$_6$)-alkyl, O—(C$_1$–C$_6$)-alkyl-O—(C$_1$–C$_3$)-alkyl;
n is from 1 to 3; and
R$^2$ is (C$_1$–C$_8$)-alkyl where one or more CH$_2$ groups in the alkyl groups may be replaced by O, CO, S, SO or SO$_2$, and alkyl may be one to trisubstituted by F, Cl, Br, CF$_3$, CN, NO$_2$, NHAc, NHBoc, NH—CO—C(CH$_3$)$_3$, hydroxyl, OCF$_3$, O—(C$_1$–C$_6$)-alkyl, COOH, CO-benzoxy, CO—O(C$_1$–C$_6$)-alkyl, tetrazole, thiazolidin-2,4-dione, indole and (C$_6$–C$_{10}$)-aryl, where thiazolidin-2,4-dione and aryl in turn maybe substituted by F, Cl, Br, CF$_3$, CN, NO$_2$, NHAc, NHTs, NHBoc, NHCbz, NH—CO—C(CH$_3$)$_3$, hydroxyl, OCF$_3$, O—(C$_1$–C$_6$)-alkyl, COOH, CO-benzoxy, CO—O(C$_1$–C$_6$)-alkyl, (C$_1$–C$_6$)-alkyl, O—(C$_1$–C$_6$)-alkyl or tetrazole;

which comprises
a) alkylation (alk-R1)
reacting cis-1,3-cyclohexanediol of the formula (II)

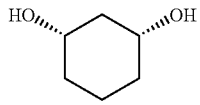

(II)

with a compound of the formula (III)

$$X^1-R^1 \quad (III)$$

where $R^1$ is as defined above and
$X^1$ is Cl, Br, I, OMs, OTs, OTf;
in the presence of bases in a suitable solvent to give a racemic compound of the formula (IV)

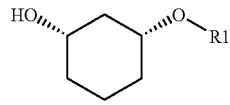

(IV)

where $R^1$ is as defined above;
b1) enzymatic ester formation (EF)+separation (S)
subjecting the resulting compounds of the formula (IV) to
stereoselective enzymatic ester formation (EF), in which the alcohols are admixed with an acyl donor and the enzyme in an organic solvent and the resulting mixture is stirred at −20 to 80° C. and, after the reaction has ended, one stereoisomer is present as an ester of the formula (V)

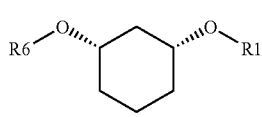

(V)

where
$R^6$ is C(=O)—($C_1$–$C_{16}$)-alkyl, C(=O)—($C_2$–$C_{16}$)-alkenyl, C(=O)—($C_3$–$C_{16}$)-alkynyl, C(=O)—($C_3$–$C_{16}$)-cycloalkyl, where one or more carbon atoms may be replaced by oxygen atoms and be substituted by 1–3 substituents from the group of F, Cl, Br, $CF_3$, CN, $NO_2$, hydroxyl, methoxy, ethoxy, phenyl and CO—O($C_1$–$C_4$)-alkyl, CO—O($C_2$–$C_4$)-alkenyl, which may in turn be substituted by 1–3 substituents from the group of F, Cl, Br, $CF_3$, and
$R^1$ is as defined above,
and the other stereoisomer is present unchanged as the alcohol of the formula (IV), and are therefore separated from each other by utilizing their different chemical or physicochemical properties (separation S) or
b2) enzymatic ester hydrolysis [=chemical esterification (CE)+enzymatic hydrolysis (EH)]+separation (S)
subjecting the resulting compound of the formula (IV) to a stereoselective enzymatic ester hydrolysis, in which the racemic alcohol is initially converted by chemical esterification (CE), for example by means of acid chloride $R^6$—Cl or acid anhydride $R^6$—O—$R^6$, in the presence of bases, to the racemic ester of the formula (V)

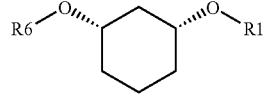

(V)

where $R^6$ and $R^1$ are each as defined above,
which, to carry out the stereoselective enzymatic ester hydrolysis (EH), is then taken up in homogeneous or heterogeneous, aqueous, aqueous-organic or organic medium, and reacted, in the presence of an enzyme in the case of hydrolysis with water and in the case of alcoholysis with an alcohol, at a temperature of 10–80° C., and after the reaction has ended, one stereoisomer is present as the alcohol of the formula (IV) and the other is present unchanged as the ester of the formula (V) and can thus be separated from each other as described under b1), and
the enantiomer of the formula (IV) occurring as an alcohol is further processed as described under d), or
c) chemical hydrolysis (CH)
hydrolyzing the enantiomer of the formula (V) occurring as an ester to the chemically enantiomeric alcohol by known methods and
d) alkylation (alk-$R^2$)
reacting further with a compound of the formula (VI)

$$R^2-X^2 \quad (VI)$$

where
$R^2$ is as defined above and
$X^2$ is Cl, Br, I, OTs, OMs, OTf;
in the presence of bases in a suitable solvent to give the compound of the formula (I).

9. The process of claim 8, wherein compounds of the formula (VI)

$$X^2-R^2 \quad (VI)$$

are used where
$X^2$ is Cl, Br, I, OMs or OTs.

10. The process of claim 9, wherein compounds of the formula (VI)

$$X^2-R^2 \quad (VI)$$

are used where
$X^2$ is Cl, Br or I.

11. The process of claim 8, wherein a compound of the formula (I)

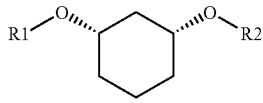

(I)

is prepared where:
$R^1$ is

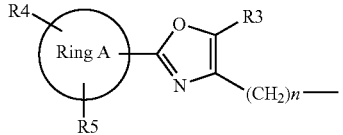

where
ring A is phenyl, 5–12 membered heteroaromatic ring which may contain from one or more heteroatoms from the group of N, O and S, fused/bicyclic 8 to 14 membered aromatic ring, ($C_3$–$C_8$)-cycloalkyl;

$R^3$ is H, $CF_3$, $(C_1-C_6)$-alkyl, $(C_3-C_8)$-cycloalkyl, phenyl;

$R^4$, $R^5$ are H, F, Br, $CF_3$, $OCF_3$, $(C_1-C_6)$-alkyl, $O-(C_1-C_6)$-alkyl;

n is from 1 to 2 and $R^2$ is $(C_1-C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—$O(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, NH—CO—$O(CH_3)_3$, hydroxyl, $OCF_3$, O—$(C_1-C_6)$-alkyl, COOH, CO-benzoxy, CO—$O(C_1-C_6)$-alkyl, $(C_1-C_6)$-alkyl, O—$(C_1-C_6)$-alkyl or tetrazole.

12. The process of claim 11, wherein a compound of the formula (I)

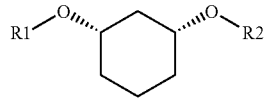
(I)

is prepared where:
$R^1$ is

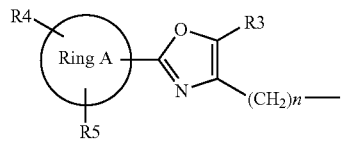

where
ring A is phenyl;
$R^3$ is $(C_1-C_4)$-alkyl;
$R^4$, $R^5$ are H, $(C_1-C_4)$-alkyl, O—$(C_1-C_4)$-alkyl;
n is 1 and
$R^2$ is $(C_1-C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—$O(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, NH—CO—$C(CH_{13})_3$, hydroxyl, $OCF_3$, O—$(C_1-C_6)$-alkyl, COOH, CO-benzoxy, CO—$O(C_1-C_6)$-alkyl, $(C_1-C_6)$-alkyl, O—$(C_1-C_6)$-alkyl or tetrazole.

13. The process as claimed in any of claims 8–12, wherein the compound of the formula (I) is (1R,3S)-2-{3-[2-(3-methoxyphenyl)-5methyloxazol-4-ylmethoxy]cyclohexyl-1-oxymethyl}-6-methylbenzoic acid.

14. The process as claimed in any of claims 8–12, wherein the compound of the formula (I) is (1R,3S)-2-{3-[2-(4-methylphenyl)-5-methyloxazol-4-ylmethoxy]cyclohexyl-1-oxymethyl}-6-methylbenzoic acid.

15. A process for preparing a chiral, nonracemic compound of the formula I

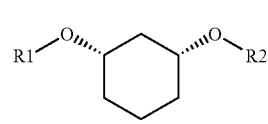
(I)

where:
$R^1$ is

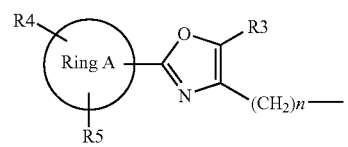

where:
ring A is phenyl, 5–12 membered heteroaromatic ring which may contain from one to four heteroatoms from the group of N, O and S, 8 to 14 membered aromatic ring, $(C_3-C_8)$-cycloalkyl;
$R^3$ is H, F, Cl, Br, OH, $NO_2$, $CF_3$, $OCF_3$, $(C_1-C_6)$-alkyl, $(C_3-C_8)$-cycloalkyl, phenyl;
$R^4$, $R^5$ are H, F, Cl, Br, OH, $NO_2$, $CF_3$, $OCF_3$, $OCF_2H$, $OCF_2$—$CF_3$, $OCF_2$—$CHF_2$, $SCF_3$, O—phenyl, $(C_1-C_6)$-alkyl, O—$(C_1-C_6)$-alkyl, O—$(C_1-C_6)$-alkyl-O—$(C_1-C_3)$-alkyl;
n is from 1 to 3; and
$R^2$ is $(C_1-C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—$O(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, NH—CO—$C(CH_3)_3$, hydroxyl, $OCF_3$, O—$(C_1-C_6)$-alkyl, COOH, CO-benzoxy, CO—$O(C_1-C_6)$-alkyl, $(C_1-C_6)$-alkyl, O—$(C_1-C_6)$-alkyl or tetrazole;

which comprises
a) alkylation (alk-PG)
reacting cis-1,3-cyclohexanediol of the formula (II)

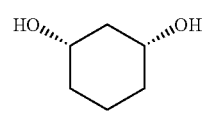
(II)

with a compound of the formula (III)

$X^1$—PG   (III)

where PG is an OH protecting group, for example benzyloxymethyl, benzyl, para-methoxybenzyl or tert-butyldimethylsilyl; and $X^1$ is Cl, Br, I, OMs, OTs, OTf;

in the presence of bases in a suitable solvent to give a racemic compound of the formula (IV)

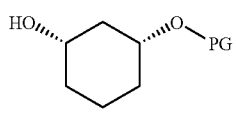

where PG is as defined above;

b1) enzymatic ester formation (EF)+separation (S)
subjecting the resulting compounds of the formula (IV) to stereoselective enzymatic ester formation (EF), in which the alcohols are admixed with an acyl donor and the enzyme in an organic solvent and the resulting mixture is stirred at −20 to 80° C. and, after the reaction has ended, one stereoisomer is present as an ester of the formula (V)

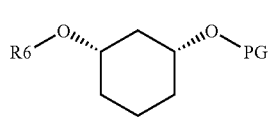

where
$R^6$ is $C(=O)—(C_1–C_{16})$-alkyl, $C(=O)—(C_2–C_{16})$-alkenyl, $C(=O)—(C_3–C_{16})$-alkynyl, $C(=O)—(C_3–C_{16})$-cycloalkyl, where one or more carbon atoms may be replaced by oxygen atoms and be substituted by 1–3 substituents from the group of F, Cl, Br, $CF_3$, CN, $NO_2$, hydroxyl, methoxy, ethoxy, phenyl and CO—O$(C_1–C_4)$-alkyl, CO—O$(C_2–C_4)$-alkenyl, which may in turn be substituted by 1–3 substituents from the group of F, Cl, Br, $CF_3$, and
PG is as defined above, and the other stereoisomer is present unchanged as the alcohol of the formula (IV), and are therefore separated from each other by utilizing their different chemical or physicochemical properties (separation S) or b2) enzymatic ester hydrolysis [=chemical esterification (CE)+enzymatic hydrolysis (EH)]+separation (S)
subjecting the resulting compound of the formula (IV) to a stereoselective enzymatic ester hydrolysis, in which the racemic alcohol is initially converted by chemical esterification (CE), for example by means of acid chloride $R^6$—Cl or acid anhydride $R^6$—O—$R^6$, in the presence of bases, to the racemic ester of the formula (V)

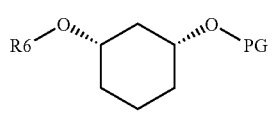

where $R^6$ and PG are each as defined above,
which, to carry out the stereoselective enzymatic ester hydrolysis (EH), is then taken up in homogeneous or heterogeneous, aqueous, aqueous-organic or organic medium, and reacted, in the presence of an enzyme in the case of hydrolysis with water and in the case of alcoholysis with an alcohol, at a temperature of 10–80° C., and after the reaction has ended, one stereoisomer is present as the alcohol of the formula (IV) and the other is present unchanged as the ester of the formula (V) and can thus be separated from each other as described under b1), and
the enantiomer of the formula (IV) occurring as an alcohol is further processed as described under d), or c) chemical hydrolysis (CH)
hydrolyzing the enantiomer of the formula (V) occurring as an ester to the chemically enantiomeric alcohol by known methods and d) alkylation (alk-$R^1$)
reacting further with a compound of the formula (VI)

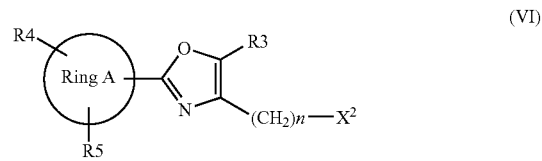

where
ring A, $R^3$, $R^4$, $R^5$ and n are each as defined above and $X^1$ is Cl, Br, I, OTs, OMs, OTf;
in the presence of bases in a suitable solvent to give the compound of the formula (Ia) as defined below, and e) detachment of the protecting group PG (detPG)
converting the compound of the formula (Ia)

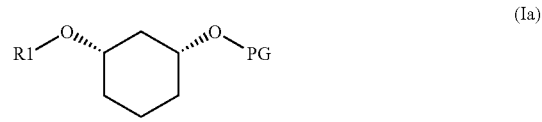

where $R^1$ and PG are each as defined above,
by detaching the protecting group by known methods to a compound of the formula (VII)

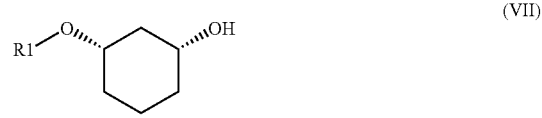

where $R^1$ is as defined above, f) alkylation (alk-$R^2$)
then reacting it with a compound of the formula (III)

$$X^1—R^2 \quad (III)$$

where $X^1$ and $R^2$ are each as defined above,
in the presence of bases in a suitable solvent to give a compound of the formula (I), the product or the enantiomeric form.

16. The process of claim 15, wherein compounds of the formula (III)

$$X^1—R^2 \quad (III)$$

are used where
$X^1$ is Cl, Br, I, OMs or OTs.

17. The process of claim 16, wherein compounds of the formula (III)

$$X^1—R^2 \quad (III)$$

are used where
$X^1$ is Cl, Br or I.

18. The process of claim 15, wherein a compound of the formula (I)

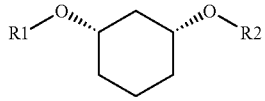 (I)

is prepared where:
R¹ is

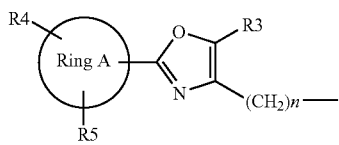

where
ring A is phenyl, 5–12 membered heteroaromatic ring which may contain from one or more heteroatoms from the group of N, O and S, fused/bicyclic 8 to 14 membered aromatic ring, $(C_3-C_8)$-cycloalkyl;
$R^3$ is H, $CF_3$, $(C_1-C_6)$-alkyl, $(C_3-C_6)$-cycloalkyl, phenyl;
$R^4$, $R^5$ are H, F, Br, $CF_3$, $OCF_3$, $(C_1-C_6)$-alkyl, O—$(C_1-C_6)$-alkyl;
n is from 1 to 2 and
$R^2$ is $(C_1-C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—O$(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, NH—CO—$C(CH_3)_3$, hydroxyl, $OCF_3$, O—$(C_1-C_6)$-alkyl, COOH, CO-benzoxy, CO—O$(C_1-C_6)$-alkyl, $(C_1-C_6)$-alkyl, O—$(C_1-C_6)$-alkyl or tetrazole.

19. The process of claim 18, wherein a compound of the formula (I)

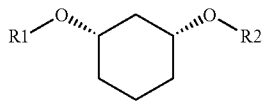 (I)

is prepared where:
R¹ is

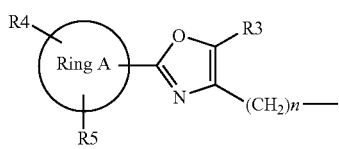

where
ring A is phenyl;
$R^3$ is $(C_1-C_4)$-alkyl;
$R^4$, $R^5$ are H, $(C_1-C_4)$-alkyl, O—$(C_1-C_4)$-alkyl;

n is 1 and
$R^2$ is $(C_1-C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—O$(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, NH—CO—$C(CH_3)_3$, hydroxyl, $OCF_3$, O—$(C_1-C_6)$-alkyl, COOH, CO-benzoxy, CO—O$(C_1-C_6)$-alkyl, $(C_1C_6)$-alkyl, O—$(C_1-C_6)$-alkyl or tetrazole.

20. The process as claimed in any of claims 15–19, wherein the compound of the formula (I) is (1R,3S)-2-{3-[2-(3-methoxyphenyl)-5-methyloxazol-4-ylmethoxy]cyclohexyl-1-oxymethyl}-6-methylbenzoic acid.

21. The process as claimed in any of claims 15–19, wherein the compound of the formula (I) is (1R,3S)-2-{3-[2-(4-methylphenyl)-5-methyloxazol-4-ylmethoxy]cyclohexyl-1-oxymethyl}-6-methylbenzoic acid.

22. A process for preparing a chiral, nonracemic compound of the formula I

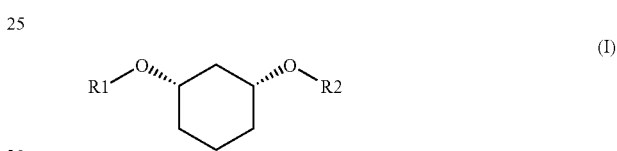 (I)

where:
R¹ is

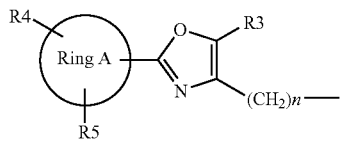

where:
ring A is phenyl, 5–12 membered heteroaromatic ring which may contain from one to four heteroatoms from the group of N, O and S, 8 to 14 membered aromatic ring, $(C_3-C_8)$-cycloalkyl;
$R^3$ is H, F, Cl, Br, OH, $NO_2$, $CF_3$, $OCF_3$, $(C_1-C_6)$-alkyl, $(C_3-C_8)$-cycloalkyl, phenyl;
$R^4$, $R^5$ are H, F, Cl, Br, OH, $NO_2$, $CF_3$, $OCF_3$, $OCF_2H$, $OCF_2$—$CF_3$, $OCF_2$—$CHF_2$, $SCF_3$, O—phenyl, $(C_1-C_6)$-alkyl, O—$(C_1-C_6)$-alkyl, O—$(C_1-C_6)$-alkyl-O—$(C_1-C_3)$-alkyl;
n is from 1 to 3; and
$R^2$ is $(C_1-C_6)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—O$(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz NH—CO—$C(CH_3)_3$, hydroxyl, $OCF_3$, O—$(C_1-C_6)$-alkyl, COOH, CO-benzoxy, CO—O$(C_1-C_6)$-alkyl, $(C_1-C_6)$-alkyl, O—$(C_1-C_6)$-alkyl or tetrazole;
which comprises a) alkylation (alk-PG)

reacting cis-1,3-cyclohexanediol of the formula (II)

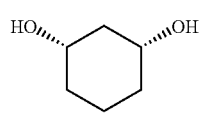
(II)

with a compound of the formula (III)

$$X^1-PG \quad (III)$$

where PG is an OH protecting group, for example benzyloxymethyl, benzyl, para-methoxybenzyl or tert-butyldimethylsilyl; and $X^1$ is Cl, Br, I, OMs, OTs, OTf;

in the presence of bases in a suitable solvent to give a racemic compound of the formula (IV)

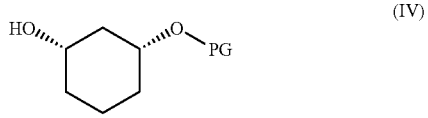
(IV)

where PG is as defined above;

b1) enzymatic ester formation (EF)+separation (S)

subjecting the resulting compounds of the formula (IV) to stereoselective enzymatic ester formation (EF), in which the alcohols are admixed with an acyl donor and the enzyme in an organic solvent and the resulting mixture is stirred at −20 to 80° C. and, after the reaction has ended, one stereoisomer is present as an ester of the formula (V)

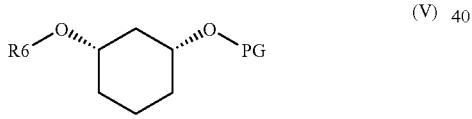
(V)

where $R^6$ is C(=O)—($C_1$–$C_{16}$)-alkyl, C(=O)—($C_2$–$C_{16}$)-alkenyl, C(=O)—($C_3$–$C_{16}$)-alkynyl, C(=O)—($C_3$–$C_{16}$)-cycloalkyl, where one or more carbon atoms may be replaced by oxygen atoms and be substituted by 1–3 substituents from the group of F, Cl, Br, $CF_3$, CN, $NO_2$, hydroxyl, methoxy, ethoxy, phenyl and CO—O($C_1$–$C_4$)-alkyl, CO—O($C_2$–$C_4$)-alkenyl, which may in turn be substituted by 1–3 substituents from the group of F, Cl, Br, $CF_3$, and PG is as defined above, and the other stereoisomer is present unchanged as the alcohol of the formula (IV), and are therefore separated from each other by utilizing their different chemical or physicochemical properties (separation S) or b2) enzymatic ester hydrolysis [=chemical esterification (CE)+enzymatic hydrolysis (EH)]+separation (S)

subjecting the resulting compound of the formula (IV) to a stereoselective enzymatic ester hydrolysis, in which the racemic alcohol is initially converted by chemical esterification (CE), for example by means of acid chloride $R^6$—Cl or acid anhydride $R^6$—O—$R^6$, in the presence of bases, to the racemic ester of the formula (V)

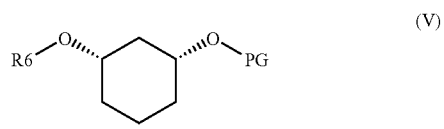
(V)

where $R^6$ and PG are each as defined above, which, to carry out the stereoselective enzymatic ester hydrolysis (EH), is then taken up in homogeneous or heterogeneous, aqueous, aqueous-organic or organic medium, and reacted, in the presence of an enzyme in the case of hydrolysis with water and in the case of alcoholysis with an alcohol, at a temperature of 10–80° C., and after the reaction has ended, one stereoisomer is present as the alcohol of the formula (IV) and the other is present unchanged as the ester of the formula (V) and can thus be separated from each other as described under b1), and the enantiomer of the formula (IV) occurring as an alcohol is further processed as described under d), or c) chemical hydrolysis (CH)

hydrolyzing the enantiomer of the formula (V) occurring as an ester to the chemically enantiomeric alcohol by known methods and d) alkylation (alk-$R^2$)

reacting further with a compound of the formula (VI)

$$R^2-X^2 \quad (VI)$$

where $R^2$ is as defined above and $X^2$ is Cl, Br, I, OTs, OMs, OTf;

in the presence of bases in a suitable solvent to give the compound of the formula (Ia) as defined below, and e) detachment of the protecting group PG (detPG)

converting the compound of the formula (Ia)

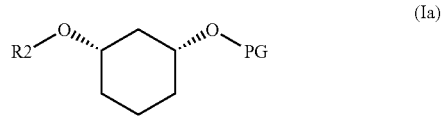
(Ia)

where $R^2$ and PG are each as defined above, by detaching the protecting group by known methods to a compound of the formula (VII)

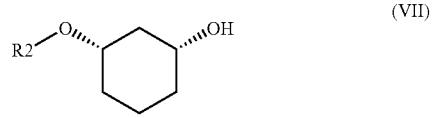
(VII)

where $R^2$ is as defined above, f) alkylation (alk-$R^1$)

then reacting it with a compound of the formula (III)

$$X^1-R^1 \quad (III)$$

where $X^1$ and $R^1$ are each as defined above, in the presence of bases in a suitable solvent to give a compound of the formula (I), the product or the enantiomeric form.

23. The process of claim 22, wherein compounds of the formula (VI)

    (VI)

are used where
X² is Cl, Br, I, OMs or OTs.

24. The process of claim 23, wherein compounds of the formula (VI)

    (VI)

are used where
X² is Cl, Br or I.

25. The process of claim 22, wherein a compound of the formula (I)

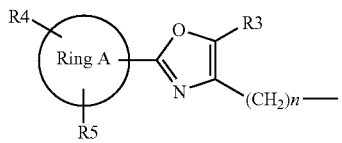    (I)

is prepared where:
R¹ is

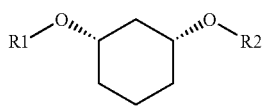

where
ring A is phenyl, 5–12 membered heteroaromatic ring which may contain from one or more heteroatoms from the group of N, O and S, fused/bicyclic 8 to 14 membered aromatic ring, $(C_3-C_8)$-cycloalkyl;
R³ is H, $CF_3$, $(C_1-C_6)$-alkyl, $(C_3-C_8)$-cycloalkyl, phenyl;
R⁴, R⁵ are H, F, Br, $CF_3$, $OCF_3$, $(C_1-C_6)$-alkyl, O—$(C_1-C_6)$-alkyl;
n is from 1 to 2 and
R² is $(C_1-C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—$O(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, NH—CO—$C(CH_3)_3$, hydroxyl, $OCF_3$, O—$(C_1-C_6)$-alkyl, COOH, CO-benzoxy, CO—$O(C_1-C_6)$-alkyl, $(C_1-C_6)$-alkyl, O—$(C_1-C_6)$-alkyl or tetrazole.

26. The process of claim 25, wherein a compound of the formula (I)

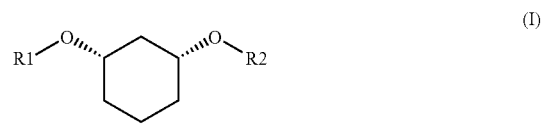    (I)

is prepared where:
R¹ is

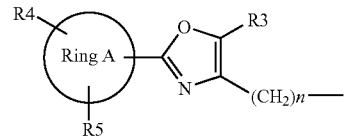

where
ring A is phenyl;
R³ is $(C_1-C_4)$-alkyl;
R⁴, R⁵ are H, $(C_1-C_4)$-alkyl, O—$(C_1-C_4)$-alkyl;
n is 1 and
R² is $(C_1-C_8)$-alkyl where one or more $CH_2$ groups in the alkyl groups may be replaced by O, CO, S, SO or $SO_2$, and alkyl may be one to trisubstituted by F, Cl, Br, $CF_3$, CN, $NO_2$, NHAc, NHBoc, NH—CO—$C(CH_3)_3$, hydroxyl, $OCF_3$, O—$(C_1-C_6)$-alkyl, COOH, CO-benzoxy, CO—$O(C_1-C_6)$-alkyl, tetrazole, thiazolidin-2,4-dione, indole and $(C_6-C_{10})$-aryl, where thiazolidin-2,4-dione and aryl in turn maybe substituted by F, Cl, Br, $CF_3$, CN, $NO_2$, NHAc, NHTs, NHBoc, NHCbz, NH—CO—$C(CH_3)_3$, hydroxyl, $OCF_3$, O—$(C_1-C_6)$-alkyl, COOH, CO-benzoxy, CO—$O(C_1-C_6)$-alkyl, $(C_1-C_6)$-alkyl, O—$(C_1-C_6)$-alkyl or tetrazole.

27. The process as claimed in any of claims 22–26, wherein the compound of the formula (I) is (1R ,3S)-2-{3-[2-(3-methoxyphenyl)-5-methyloxazol-4-ylmethoxy]cyclohexyl-1-oxymethyl}-6-methylbenzoic acid.

28. The process as claimed in any of claims 22–26, wherein the compound of the formula (I) is (1R,3S)-2-{3-[2-(4-methylphenyl)-5-methyloxazol-4-ylmethoxy]cyclohexyl-1-oxymethyl}-methylbenzoic acid.

* * * * *